US012426891B2

(12) United States Patent
Sjostrom et al.

(10) Patent No.: US 12,426,891 B2
(45) Date of Patent: Sep. 30, 2025

(54) DEVICES AND METHODS FOR APPLYING A HEMOSTATIC CLIP ASSEMBLY

(71) Applicant: Conmed Corporation, Largo, FL (US)

(72) Inventors: Doug Sjostrom, Tewksbury, MA (US); Michael Barenboym, Boston, MA (US); Daniel P. Damato, Boston, MA (US)

(73) Assignee: Conmed Corporation, Largo, FL (US)

( * ) Notice: Subject to any disclaimer, the term of this patent is extended or adjusted under 35 U.S.C. 154(b) by 617 days.

(21) Appl. No.: 17/773,843

(22) PCT Filed: Nov. 2, 2020

(86) PCT No.: PCT/US2020/058556
§ 371 (c)(1),
(2) Date: May 2, 2022

(87) PCT Pub. No.: WO2021/087464
PCT Pub. Date: May 6, 2021

(65) Prior Publication Data
US 2023/0055309 A1    Feb. 23, 2023

Related U.S. Application Data
(60) Provisional application No. 62/929,187, filed on Nov. 1, 2019.

(51) Int. Cl.
*A61B 17/128* (2006.01)
*A61B 17/00* (2006.01)
*A61B 17/122* (2006.01)

(52) U.S. Cl.
CPC ........ *A61B 17/1285* (2013.01); *A61B 17/122* (2013.01); *A61B 2017/003* (2013.01); *A61B 2017/00473* (2013.01)

(58) Field of Classification Search
CPC .............. A61B 17/1285; A61B 17/122; A61B 2017/003; A61B 2017/00473;
(Continued)

(56) References Cited

U.S. PATENT DOCUMENTS

| 4,651,737 A | 3/1987 | Deniega |
| 5,626,607 A | 5/1997 | Malecki et al. |

(Continued)

FOREIGN PATENT DOCUMENTS

| CN | 102727276 A | 10/2012 |
| CN | 203539404 U | 4/2014 |

(Continued)

OTHER PUBLICATIONS

China National Intellectual Property Administration, First Office Action issued on Jul. 19, 2024, in corresponding Chinese Patent Application No. 202080083498.6, 20 pages.

(Continued)

*Primary Examiner* — Andrew Restaino
(74) *Attorney, Agent, or Firm* — Troutman Pepper Locke LLP; Scott D. Wofsy; Michael J. Pollack

(57) ABSTRACT

A proximal delivery catheter includes a proximal handle assembly, an elongated catheter body defining a longitudinal axis and extending distally from the proximal handle assembly, and a drive wire movably positioned within the elongated catheter body. A release pin assembly is coupled to a distal end of the drive wire. The release pin assembly including a release pin and a release pin housing positioned outward from the release pin. A shaft spring is positioned outward from the release pin housing. The shaft spring includes an annular portion wherein the release pin housing is configured and adapted to interfere with the annular portion of the shaft spring. A distal clip assembly is removably connected to the distal end of the elongated catheter (Continued)

body. The proximal delivery catheter is configured to transmit linear motion along and torsion about the longitudinal axis to at least a portion of the distal clip assembly.

23 Claims, 18 Drawing Sheets

(58) Field of Classification Search
CPC .. A61B 2017/00477; A61B 2017/2936; A61B 2090/037; A61B 2090/0807
See application file for complete search history.

(56) References Cited

U.S. PATENT DOCUMENTS

| | | |
|---|---|---|
| 5,749,881 A | 5/1998 | Sackier et al. |
| 5,766,184 A | 6/1998 | Matsuno et al. |
| 5,766,189 A | 6/1998 | Matsuno |
| 6,464,710 B1 | 10/2002 | Foster |
| 7,094,245 B2 | 8/2006 | Adams et al. |
| 7,452,327 B2 | 11/2008 | Durgin et al. |
| 7,494,461 B2 | 2/2009 | Wells et al. |
| 7,879,052 B2 | 2/2011 | Adams et al. |
| 8,083,668 B2 | 12/2011 | Durgin et al. |
| 8,088,061 B2 | 1/2012 | Wells et al. |
| 8,162,959 B2 | 4/2012 | Cohen et al. |
| 8,444,660 B2 | 5/2013 | Adams et al. |
| 8,545,519 B2 | 10/2013 | Aguirre et al. |
| 8,551,119 B2 | 10/2013 | Kogiso et al. |
| 8,663,247 B2 | 3/2014 | Menn et al. |
| 8,685,048 B2 | 4/2014 | Adams et al. |
| 8,709,027 B2 | 4/2014 | Adams et al. |
| 8,771,293 B2 | 7/2014 | Surti et al. |
| 8,845,658 B2 | 9/2014 | Adams |
| 8,858,588 B2 | 10/2014 | Sigmon, Jr. et al. |
| 8,915,837 B2 | 12/2014 | Wells et al. |
| 8,939,997 B2 | 1/2015 | Martinez et al. |
| 8,974,371 B2 | 3/2015 | Durgin et al. |
| 8,979,891 B2 | 3/2015 | McLawhorn et al. |
| 9,271,731 B2 | 3/2016 | Adams et al. |
| 9,332,988 B2 | 5/2016 | Adams et al. |
| 9,339,270 B2 | 5/2016 | Martinez et al. |
| 9,370,371 B2 | 6/2016 | Durgin et al. |
| 9,375,219 B2 | 6/2016 | Surti et al. |
| 9,445,821 B2 | 9/2016 | Wells et al. |
| 9,480,478 B2 | 11/2016 | Adams |
| 9,743,933 B2 | 8/2017 | Phillips-Hungerford et al. |
| 9,775,590 B2 | 10/2017 | Ryan et al. |
| 9,795,390 B2 | 10/2017 | Jin et al. |
| 9,895,154 B2 | 2/2018 | Cohen et al. |
| 9,955,977 B2 | 5/2018 | Martinez et al. |
| 9,980,725 B2 | 5/2018 | Durgin et al. |
| 9,987,018 B2 | 6/2018 | Surti et al. |
| 10,010,336 B2 | 7/2018 | Martinez et al. |
| 10,143,479 B2 | 12/2018 | Adams et al. |
| 10,154,842 B2 | 12/2018 | Wells et al. |
| 10,166,028 B2 | 1/2019 | Menn et al. |
| 10,172,623 B2 | 1/2019 | Adams et al. |
| 10,172,624 B2 | 1/2019 | Adams et al. |
| 10,307,169 B2 | 6/2019 | Wells et al. |
| 10,335,159 B2 | 7/2019 | Naveed et al. |
| 10,537,314 B2 | 1/2020 | Ryan et al. |
| 10,548,612 B2 | 2/2020 | Martinez et al. |
| 10,575,857 B2 | 3/2020 | King et al. |
| 10,588,635 B2 | 3/2020 | Smith et al. |
| 10,595,877 B2 | 3/2020 | Menn et al. |
| 10,624,642 B2 | 4/2020 | Randhawa |
| 10,646,230 B2 | 5/2020 | Phillips-Hungerford et al. |
| 10,786,254 B2 | 9/2020 | Wells et al. |
| 10,792,046 B2 | 10/2020 | Martinez et al. |
| 10,813,650 B2 | 10/2020 | Surti et al. |
| 10,820,904 B2 | 11/2020 | Ryan et al. |
| 10,835,261 B2 | 11/2020 | Menn et al. |
| 10,905,434 B2 | 2/2021 | Estevez et al. |
| 10,952,725 B2 | 3/2021 | Durgin et al. |
| 10,952,742 B2 | 3/2021 | Lehtinen et al. |
| 10,952,743 B2 | 3/2021 | Adams et al. |
| 11,020,125 B2 | 6/2021 | Randhawa et al. |
| 11,045,194 B2 | 6/2021 | King et al. |
| 11,071,552 B2 | 7/2021 | Saenz Villalobos et al. |
| 11,083,465 B2 | 8/2021 | Ryan et al. |
| 11,129,623 B2 | 9/2021 | Saenz Villalobos et al. |
| 11,129,624 B2 | 9/2021 | Martinez et al. |
| 11,202,637 B2 | 12/2021 | Murray et al. |
| 11,253,259 B2 | 2/2022 | Smith et al. |
| 11,399,835 B2 | 8/2022 | Congdon et al. |
| 11,426,177 B2 | 8/2022 | Congdon et al. |
| 2002/0045909 A1 | 4/2002 | Kimura et al. |
| 2006/0155308 A1 | 7/2006 | Griego |
| 2008/0140089 A1* | 6/2008 | Kogiso ............... A61B 17/1285 606/142 |
| 2008/0208217 A1 | 8/2008 | Adams |
| 2008/0306491 A1 | 12/2008 | Cohen et al. |
| 2010/0152753 A1* | 6/2010 | Menn .................. A61B 17/083 606/158 |
| 2010/0268254 A1 | 10/2010 | Golden et al. |
| 2012/0065646 A1 | 3/2012 | Phillips-Hungerford et al. |
| 2014/0249551 A1 | 9/2014 | Adams et al. |
| 2014/0257342 A1 | 9/2014 | Adams et al. |
| 2014/0364874 A1 | 12/2014 | Adams |
| 2016/0128698 A1 | 5/2016 | Adams et al. |
| 2016/0143644 A1 | 5/2016 | Adams et al. |
| 2016/0213378 A1 | 7/2016 | Adams et al. |
| 2016/0220260 A1 | 8/2016 | Martinez et al. |
| 2016/0367258 A1* | 12/2016 | Jin ..................... A61B 17/1285 |
| 2017/0156785 A1* | 6/2017 | Smith ................ A61B 18/1206 |
| 2017/0325823 A1 | 11/2017 | Phillips-Hungerford et al. |
| 2018/0049745 A1 | 2/2018 | Randhawa et al. |
| 2018/0085122 A1 | 3/2018 | Ryan et al. |
| 2018/0125497 A1 | 5/2018 | Cohen et al. |
| 2018/0140300 A1* | 5/2018 | Randhawa ............ A61B 17/10 |
| 2018/0193021 A1 | 7/2018 | Martinez et al. |
| 2018/0235608 A1 | 8/2018 | Durgin et al. |
| 2019/0053804 A1 | 2/2019 | Wells et al. |
| 2019/0059905 A1 | 2/2019 | Adams et al. |
| 2019/0083099 A1 | 3/2019 | Adams et al. |
| 2019/0083100 A1 | 3/2019 | Menn et al. |
| 2019/0090883 A1 | 3/2019 | Adams et al. |
| 2019/0150929 A1 | 5/2019 | Gregan et al. |
| 2019/0223875 A1 | 7/2019 | Saenz Villalobos et al. |
| 2019/0247049 A1 | 8/2019 | Wells et al. |
| 2020/0138444 A1 | 5/2020 | Martinez et al. |
| 2020/0146686 A1 | 5/2020 | Haack et al. |
| 2020/0163676 A1 | 5/2020 | Menn et al. |
| 2020/0214707 A1 | 7/2020 | Randhawa |
| 2021/0022747 A1 | 1/2021 | Menn et al. |
| 2022/0175386 A1 | 6/2022 | Martinez et al. |

FOREIGN PATENT DOCUMENTS

| | | |
|---|---|---|
| CN | 104248461 A | 12/2014 |
| CN | 104546055 A | 4/2015 |
| CN | 204364061 U | 6/2015 |
| CN | 107684448 A | 2/2018 |
| CN | 109009310 A | 12/2018 |
| CN | 109640841 A | 4/2019 |
| CN | 110141295 A | 8/2019 |
| CN | 209884245 U | 1/2020 |
| EP | 3476307 A1 | 5/2019 |
| EP | 3643255 A1 | 4/2020 |
| EP | 3763298 A1 | 1/2021 |
| WO | 9915089 A1 | 4/1999 |
| WO | 2015176361 A1 | 11/2015 |
| WO | 2016184120 A1 | 11/2016 |
| WO | 2020/186838 A1 | 9/2020 |
| WO | 2021/087461 A2 | 5/2021 |
| WO | 2021/087464 A2 | 5/2021 |
| WO | 2022/076032 A1 | 4/2022 |

(56) References Cited

FOREIGN PATENT DOCUMENTS

| WO | 2022/076033 A1 | 4/2022 |
| WO | 2022/260751 A1 | 12/2022 |

OTHER PUBLICATIONS

International Search Report and Written Opinion for PCT Application No. PCT/US2020/058553, dated May 3, 2021, 24 pages.
International Search Report and Written Opinion for PCT Application No. PCT/US2020/058556, dated Jul. 9, 2021, 19 pages.
International Search Report and Written Opinion for International Patent Application PCT/US2021/030246, dated Sep. 30, 2021, 17 pages.
International Search Report and Written Opinion for International Patent Application PCT/US2021/030263, dated Oct. 11, 2021, 17 pages.
International Search Report and Written Opinion for PCT Application No. PCT/US2022/024654, dated Sep. 20, 2022, 18 pages.

* cited by examiner

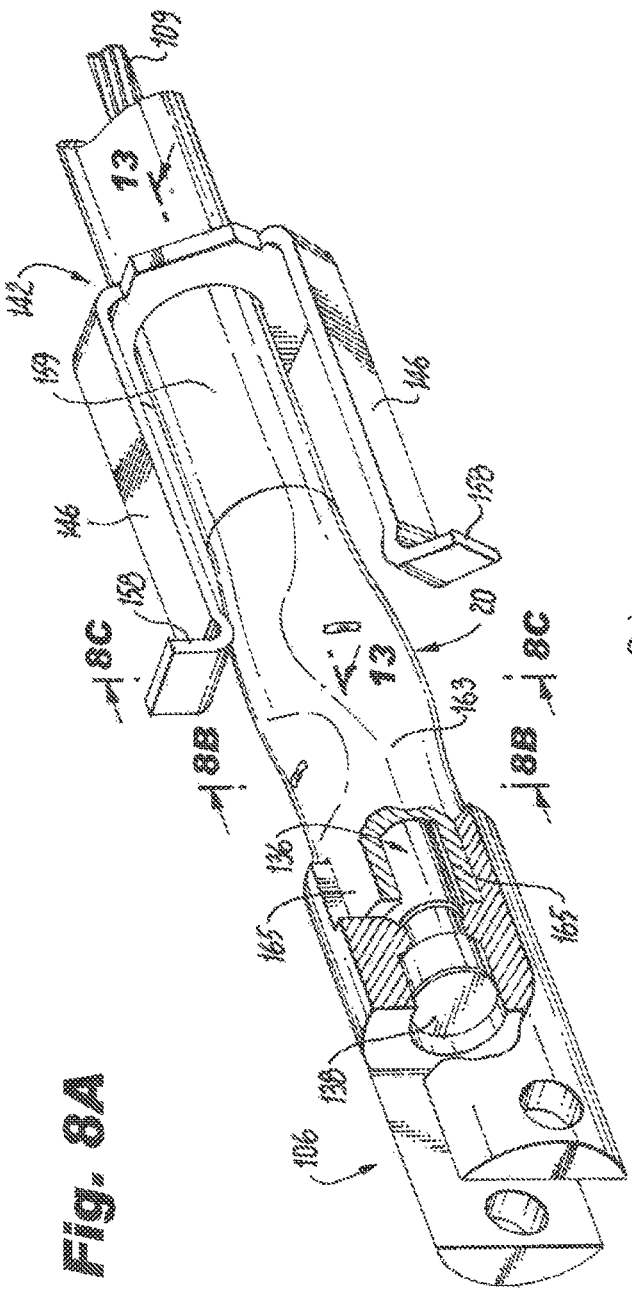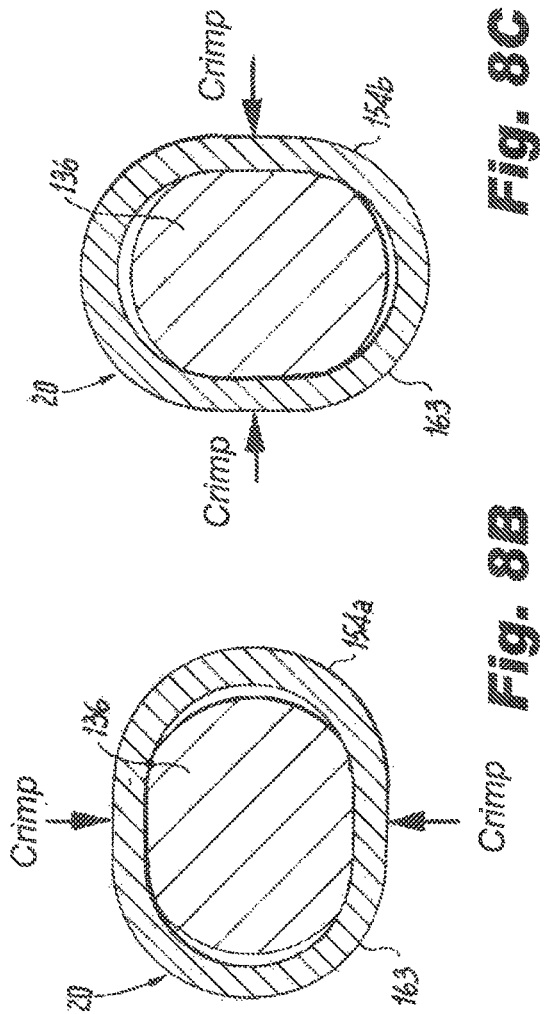

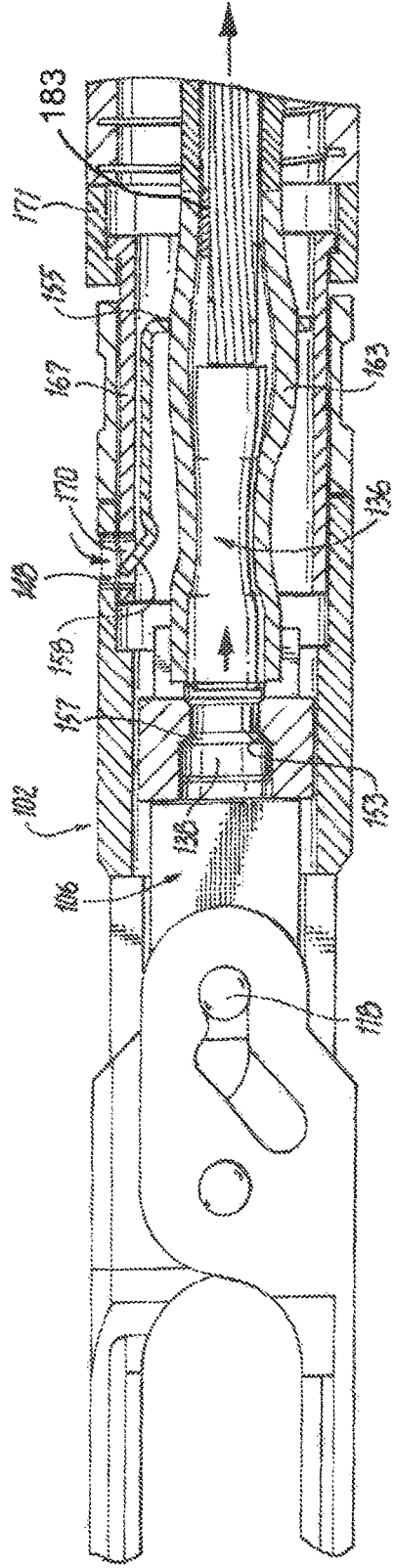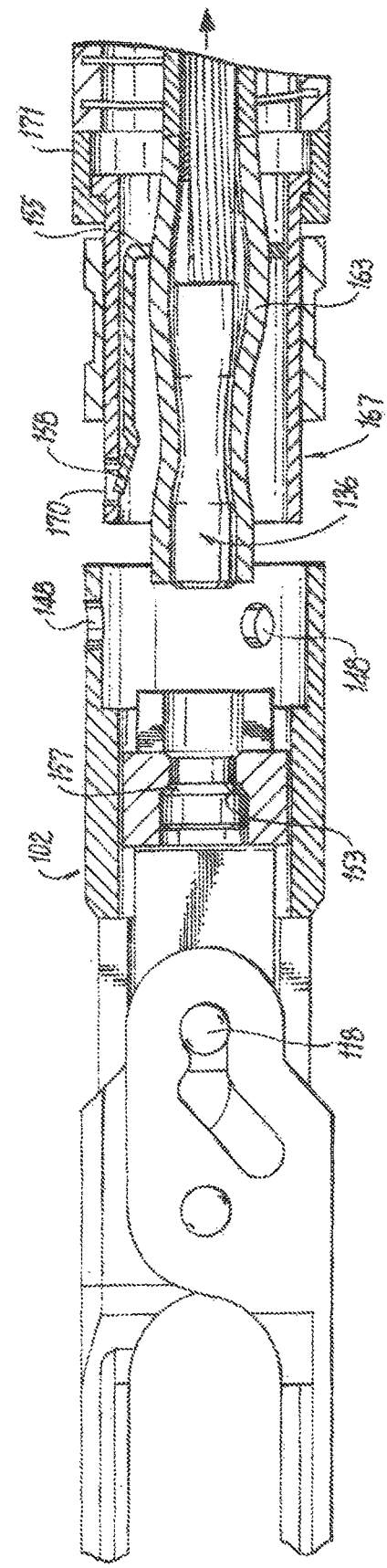
Fig. 19
Fig. 20

DEVICES AND METHODS FOR APPLYING A HEMOSTATIC CLIP ASSEMBLY

CROSS-REFERENCE TO RELATED APPLICATION

This Application is a U.S. National Stage application under 35 U.S.C. 371 of International Application No. PCT/US2020/058556 filed Nov. 2, 2020, which claims the benefit of priority to U.S. Provisional Patent Application Ser. No. 62/929,187 filed Nov. 1, 2019, the disclosure of which is herein incorporated by reference in its entirety.

BACKGROUND OF THE INVENTION

1. Field of the Invention

The subject invention is directed to surgical equipment, and more particularly to hemostatic clips used endoscopic surgical procedures.

2. Description of Related Art

Endoscopic or "minimally invasive" hemostatic clips are used in performance of hemostasis to stop and prevent re-bleeding, or in procedures such as ampullectomies, tissue repair and correction of other tissue defects. Such procedures are typically performed by grasping the tissue with the hemostatic clip. Benefits of using hemostatic clips in such procedures include reduced trauma to the patient, low re-bleeding rate, reduced opportunity for infection, and decreased recovery time.

The subject invention provides an improved mechanism for a hemostatic clip. The novel design allows for a shorter deployed clip body, improved tissue grasping and clip locking, and an improved disconnecting feature, which are described in detail herein below, along with other novel devices and systems.

SUMMARY OF THE DISCLOSURE

The subject invention is directed to a new and useful device for applying a hemostatic clip assembly. The device includes a proximal delivery catheter including a proximal handle assembly and an elongated catheter body extending distally from the proximal handle assembly. The elongated catheter body defining a longitudinal axis. The device includes a distal clip assembly removably connected to a distal end of the elongated catheter body. The distal clip assembly includes a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members. The proximal delivery catheter is configured and adapted to transmit linear motion along the longitudinal axis and torsion about the longitudinal axis to at least a portion of the distal clip assembly. At least one of the jaw members is configured and adapted to rotate about the first pin between an open configuration and a closed configuration.

In some embodiments, the distal clip housing includes a pair of spaced apart arms defining a slot configured and adapted to provide clearance for respective proximal portions of the jaw members to rotate relative the first pin. The distal clip assembly can include a second pin connecting between the jaw members and the jaw adapter yoke. Each jaw member can include a proximal body portion and a distal end effector. The proximal body portion of each jaw member can include a respective cam slot configured and adapted to receive the second pin and a pivot aperture configured and adapted to receive the first pin. The second pin can be configured and adapted to translate within the cam slots to move axially relative to the distal clip housing and the jaw assembly to move the jaw members between the open configuration, where respective distal tips of the jaw members are moved away from one another, the closed configuration where the respective distal tips of the jaw members are approximated towards one another to grasp tissue, and a locked configuration.

Each cam slot can define a distal portion and a proximal portion. The distal portion of each cam slot can be angled relative to the proximal portion of each cam slot. The proximal portion of each cam slot can define a proximal axis extending in a first direction, the distal portion of each cam slot can define a distal axis extending at an oblique angle relative to the proximal axis, and the distal axes of each cam slot can be positioned at opposite angles relative to one another. Each cam slot can include a proximal locking neck projecting into the cam slot defining a proximal locking area. The jaw members can be in the locked configuration when the second pin is proximal relative to the proximal locking neck in the proximal locking area. The proximal locking neck can include at least one of a protrusion projecting into the cam slot or a tapered portion.

The jaw adapter yoke can include a proximal receiving portion and the proximal delivery catheter can include a release pin having a distal portion configured and adapted to be received within the proximal receiving portion of the jaw adapter yoke to transmit axial and rotational force to the jaw adapter yoke. The proximal delivery catheter can include a drive wire coupled to a proximal portion of the release pin to transmit linear and rotational motion from the drive wire to the jaw adapter yoke. The proximal handle assembly can include an actuation portion coupled to a proximal end of the drive wire, and a grasping portion. The actuation portion is configured and adapted to translate relative to the grasping portion to apply axial force to the drive wire.

The proximal delivery catheter can include a shaft spring between a proximal end of the distal clip assembly and the distal end of the catheter body. The shaft spring can include at least one arm removably coupled to the distal clip housing. The at least one arm can include an outwardly extending flange that removably engages with an aperture defined in the proximal end of the distal clip housing. The proximal delivery catheter can include a release pin releasably connected to the jaw adapter yoke, and a release pin housing positioned around the release pin. An annular portion of the shaft spring can be positioned around the release pin housing. The release pin can be configured and adapted to interfere with the annular portion of the shaft spring as the release pin housing moves proximally to move the shaft spring proximally relative to the distal clip housing and release the outwardly extending flange of the at least one arm from the aperture of the distal clip housing. The release pin housing can have at least one non-circular cross-section portion and the annular portion of the shaft spring can be proximal to the at least one non-circular cross-section portion. The non-circular cross-section portion can be configured and adapted to interfere with the annular portion of the shaft spring upon proximal translation of the release pin housing.

The release pin has a distal portion, a proximal portion, and a neck portion therebetween. The distal portion of the release pin can be configured and adapted to be received within a bore of the jaw adapter yoke to transmit axial force to the jaw adapter yoke. The neck portion of the release pin can be configured and adapted to shear when an axial force is applied to the release pin in a proximal direction, thereby separating the distal portion from the proximal portion and releasing the proximal portion of the release pin from the distal clip assembly. The neck portion of the release pin can have a smaller diameter than the proximal portion of the release pin and the distal portion of the release pin, thereby configured and adapted to create a stress concentration to limit elongation during a shear. The release pin can include a silver material.

In accordance with another aspect, a proximal delivery catheter includes a proximal handle assembly, an elongated catheter body defining a longitudinal axis and extending distally from the proximal handle assembly, and a drive wire movably positioned within the elongated catheter body. A release pin assembly is coupled to a distal end of the drive wire. The release pin assembly including a release pin and a release pin housing positioned outward from the release pin. A shaft spring is positioned outward from the release pin housing. The shaft spring includes an annular portion wherein the release pin housing is configured and adapted to interfere with the annular portion of the shaft spring upon proximal translation of the release pin housing. A distal clip assembly is removably connected to the distal end of the elongated catheter body. The proximal delivery catheter is configured to transmit linear motion along and torsion about the longitudinal axis to at least a portion of the distal clip assembly.

The release pin, release pin housing, shaft spring and drive wire are similar to those described above. The distal clip assembly can include a distal clip housing, a jaw assembly having a pair of cooperating jaw members fixed to the distal clip housing by a first pin, and a jaw adapter yoke operatively connected to the jaw members, as previously described. A proximal body portion of each jaw member can include a respective cam slot, like cam slots described above. The distal clip housing can include a pair of spaced apart arms, like those described above. The distal clip assembly can include a second pin like that described above. Each cam slot can include a proximal locking neck projecting into the cam slot defining a proximal locking area, similar to the proximal locking neck and proximal locking area described above. Each cam slot can define a distal portion and a proximal portion, as previously described. The proximal handle assembly can include an actuation portion and a grasping portion, as described above.

In accordance with another aspect, a method for firing a hemostatic clip includes positioning a distal clip assembly proximate to a target location. The distal clip assembly includes a distal clip housing, a jaw assembly having a pair of cooperating jaw members fixed to the distal clip housing by a first pin, and a jaw adapter yoke operatively connected to the jaw members. The method includes translating an actuation portion of a proximal handle assembly of a proximal delivery catheter relative to a grasping portion of the proximal handle assembly in at least one of a proximal direction or a distal direction. The proximal delivery catheter includes an elongated catheter body extending distally from the proximal handle assembly. The elongated catheter body defines a longitudinal axis. The actuation portion is operatively connected to the jaw adapter yoke via a drive wire to transmit linear motion along the longitudinal axis and torsion about the longitudinal axis to the jaw adapter yoke. The linear motion of the jaw adapter yoke transmits the linear motion to a second pin positioned within a cam slot of at least one jaw member, thereby rotating at least one of the jaw members about the first pin between an open configuration and a closed configuration.

In some embodiments, translating the actuation portion includes translating the actuation portion in the proximal direction to transmit the linear motion in the proximal direction to the second pin to lock the second pin behind a lock protrusion of the cam slot to lock at least one of the jaw members in a locked configuration. Translating the actuation portion can include translating the actuation portion further in the proximal direction to transmit further linear motion in the proximal direction to a release pin coupled to the drive wire, the axial force on the release pin in the proximal direction shearing the release pin at a neck portion, thereby separating a proximal portion of the release pin from a proximal portion of a jaw adapter yoke.

In some embodiments, the axial force on the release pin in the proximal direction causes interference between a release pin housing with an annular portion of a shaft spring causing the shaft spring to move proximally relative to the distal clip housing and release an outwardly extending flange of at least one arm of the shaft spring from an aperture of the distal clip housing. Translating the drive wire in the proximal direction can include translating a jaw adapter yoke in the proximal direction. Translating the actuation portion of the proximal delivery catheter can include translating the actuation portion in the distal direction to transmit the axial force in the distal direction to the second pin causing the at least one jaw to rotate about the first pin to the open configuration.

In accordance with another aspect, a hemostatic clip assembly includes a distal clip housing defining a longitudinal axis, a jaw assembly having a pair of cooperating jaw members fixed to the distal clip housing by a first pin, the first pin oriented orthogonally relative to the longitudinal axis, and a jaw adapter yoke operatively connected to the jaw members. The jaw adapter yoke is configured and adapted to translate axially along the longitudinal axis and rotate about the longitudinal axis. At least one of the jaw members is configured and adapted to rotate about the first pin between an open configuration and a closed configuration.

The distal clip housing can include a pair of spaced apart arms, similar to those described above. The hemostatic clip assembly can include a second pin, similar to that described above. Each jaw member and its respective cam slot can be similar to those described above.

These and other features of the hemostatic clip of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the gas circulation system of the subject invention without undue experimentation, preferred embodiments thereof will be described in detail herein below with reference to the figures wherein:

FIG. 8A is a perspective view of a portion of the device of FIG. 1 with a partial cut-away, showing the release pin mating with the jaw adapter yoke and the release pin housing;

FIGS. 8B and 8C are schematic cross-sectional front elevation views of a portion of the device of FIG. 1, showing the non-circular cross-sections of the release pin and release pin housing at the distal crimp (FIG. 8B) and the non-circular cross-section of the release pin housing at the proximal crimp (FIG. 8C);

FIG. 19 is a partial cross-sectional side elevation view of a portion of the device of FIG. 1, showing the jaw members in the locked configuration where the second pin is proximal relative to a proximal locking neck where the release pin is shearing to release the distal clip assembly;

FIG. 20 is a partial cross-sectional side elevation view of a portion of the device of FIG. 1, showing the flanges of the shaft spring deformed and released from the apertures of the distal clip housing and the shaft bearing;

DETAILED DESCRIPTION OF THE PREFERRED EMBODIMENTS

Figure 1:
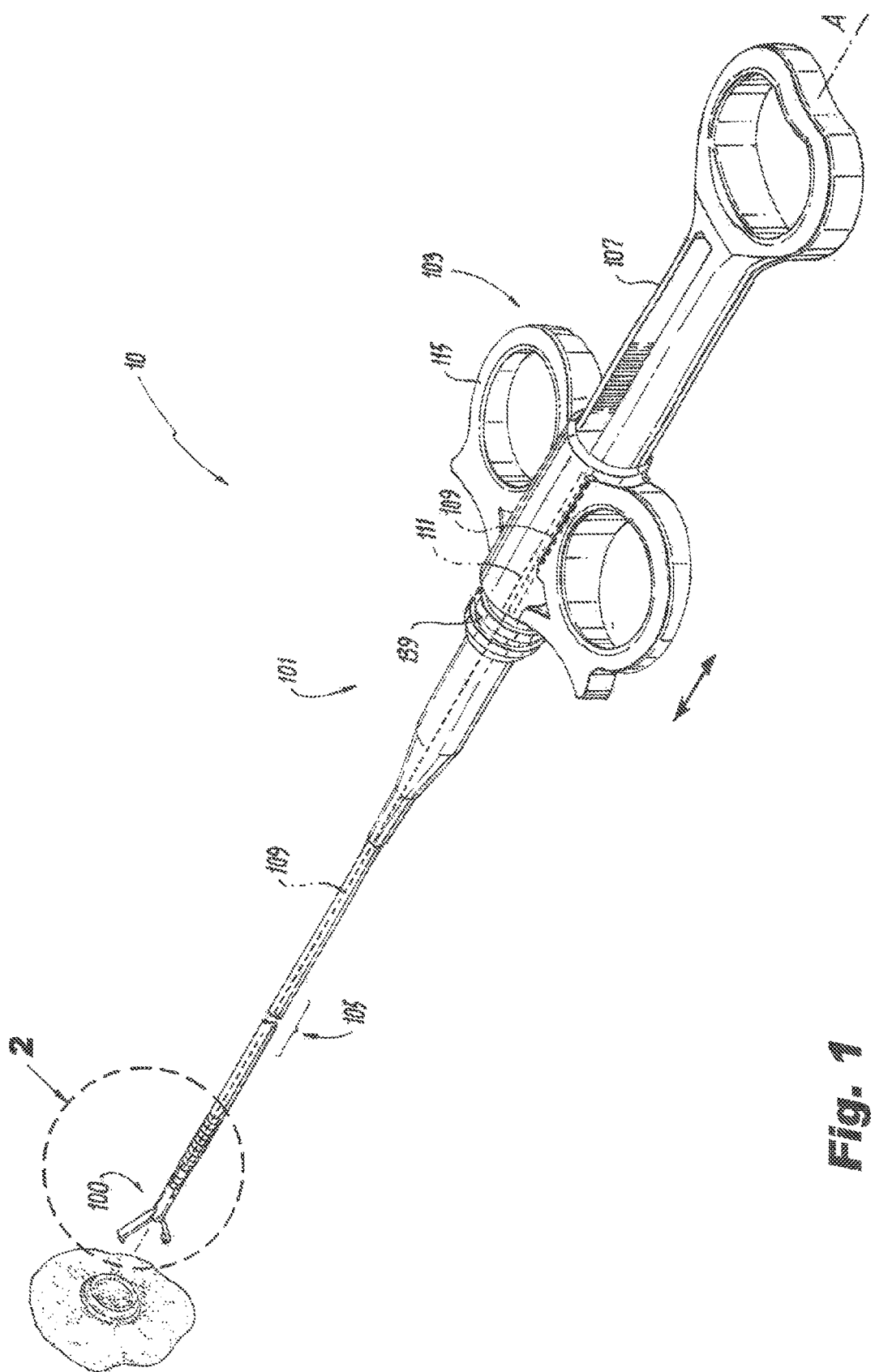
FIG. 1 is a perspective view from the proximal direction of a device for applying a hemostatic clip assembly constructed in accordance with an embodiment of the present disclosure, showing a proximal delivery catheter having a proximal handle assembly and an elongated catheter body and the distal clip assembly.

Referring now to the drawings wherein like reference numerals identify similar structural elements and features of the subject invention, there is illustrated in FIG. 1 a gas circulation system for performing an endoscopic surgical procedure in a surgical cavity of a patient, and more particularly, for performing a robotically assisted laparoscopic surgical procedure in the abdominal cavity of a patient that is constructed in accordance with a preferred embodiment of the subject disclosure and is designated generally by reference numeral 10.

Figure 2:
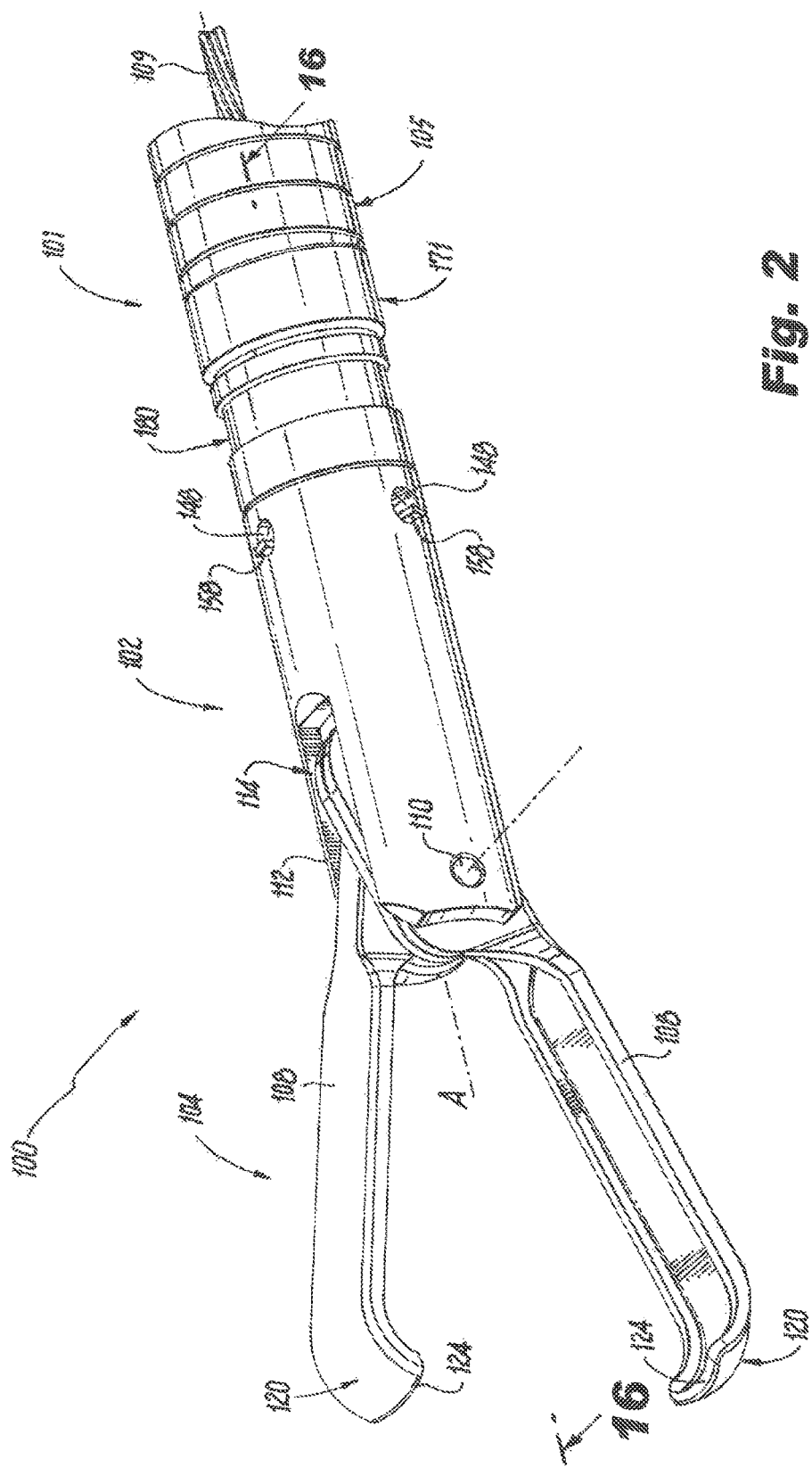
FIG. 2 is a perspective view of the distal clip assembly of FIG. 1, showing a jaw assembly with a pair of cooperating jaw members fixed to the distal clip housing by a first pin.

As shown in FIGS. 1-2, a surgical device 10 for applying a hemostatic clip assembly 100 includes proximal delivery catheter 101 and the distal clip assembly 100. The distal clip assembly 100, e.g. a hemostasis clip, separates from the delivery catheter 101 to function as a short-term implant to stop and prevent re-bleeding, or in procedures such as ampullectomies, tissue repair and correction of other tissue defects. Such procedures are typically performed by grasping the tissue with the hemostatic clip. Using hemostatic clips in such procedures can result in benefits such as reduced trauma to the patient, low re-bleeding rate, reduced opportunity for infection, and decreased recovery time.

With continued reference to FIGS. 1-2, the proximal delivery catheter 101 has a proximal handle assembly 103 and an elongated catheter body 105 extending distally from the proximal handle assembly 103. The elongated catheter body 105 defines a longitudinal axis A. The proximal handle assembly 103 includes an actuation portion 115 coupled to a proximal end 111 of the drive wire 109, and a grasping portion 107. The actuation portion 115 is configured and adapted to translate along the longitudinal axis A, relative to the grasping portion 107, to apply an axial force to the drive wire 109. Grasping portion 107 and actuation portion 115 are configured and adapted to rotate relative to a cap 139 and catheter body 105, thereby also rotating drive wire 109. Internal annular slots on the distal portion of grasping portion 107 interact with annular tabs on inside diameter of end cap 139 to prevent axial motion of actuation portion 115 and grasping portion 107 but allow rotation.

Figure 3:
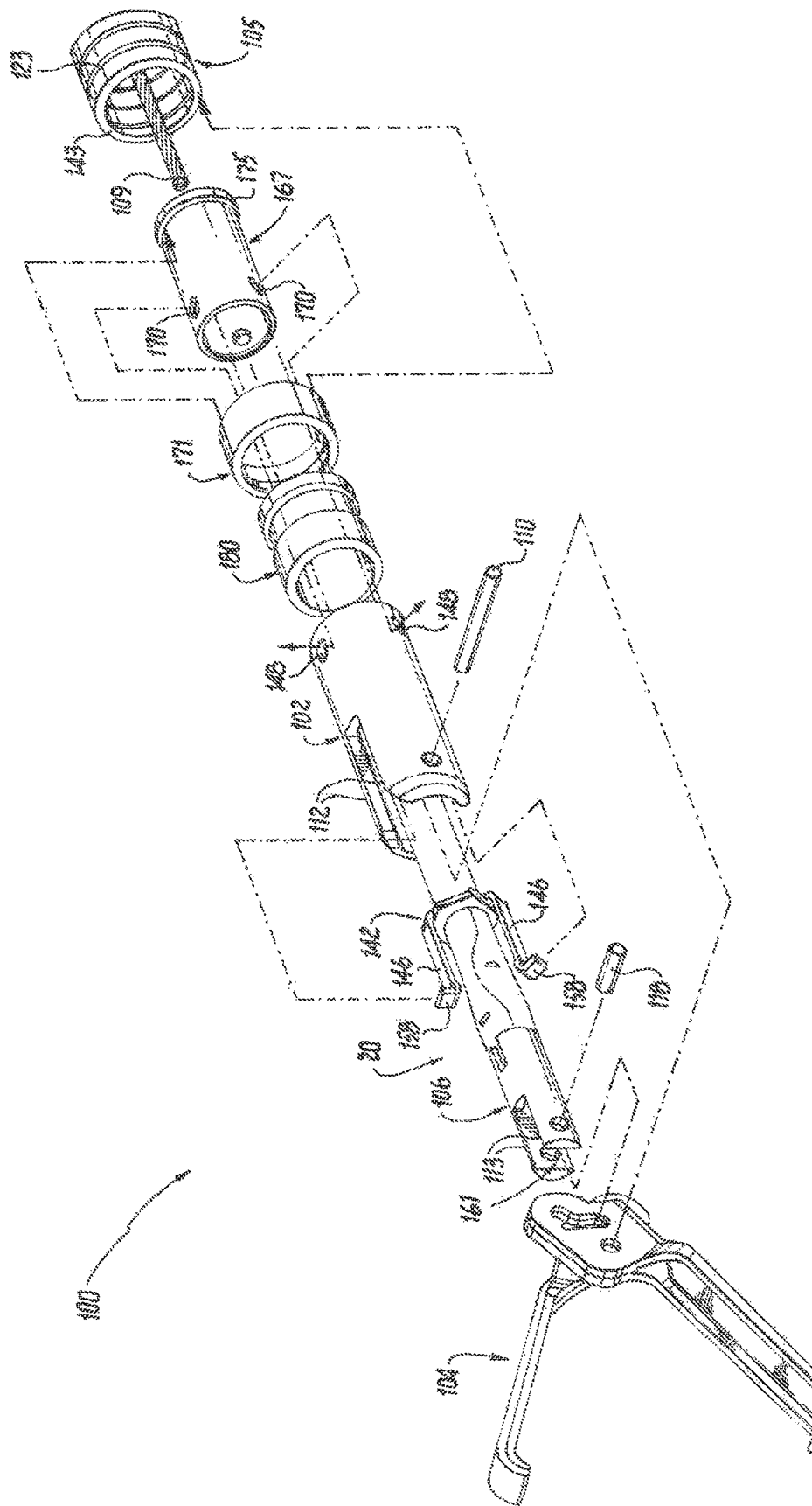
FIG. 3 is an exploded perspective view of a portion of the device of FIG. 1, showing the showing the distal end of the proximal delivery catheter and the distal clip assembly.

With reference now to FIGS. 2-3, the proximal delivery catheter 101 includes a shaft spring 142 between a proximal end of the distal clip assembly 100 and a distal end of the catheter body 105. The distal clip assembly 100 includes a distal clip housing 102 and a jaw assembly 104 pivotally connected to the distal clip housing 102. The proximal delivery catheter 101 includes a shaft bearing 167 coupled to the distal clip housing 102 via the shaft spring 142, and a bearing ring 171 mated with a proximal end of the shaft bearing 167. The jaw assembly 104 has a pair of cooperating jaw members 108 fixed to the distal clip housing 102 by a first pin 110. The first pin 110 is oriented orthogonally relative to the longitudinal axis A. The shaft spring 142 includes arms 146 configured and adapted to be removably coupled to the distal clip housing 102, described in more detail below. The hemostatic clip assembly 100 is removably connected to a distal end 143 of the elongated catheter body 105 via the shaft spring 142. The proximal delivery catheter 101 is configured and adapted to transmit linear motion along the longitudinal axis A and torsion about the longitudinal axis A to at least a portion of the distal clip assembly 100.

Figure 4:
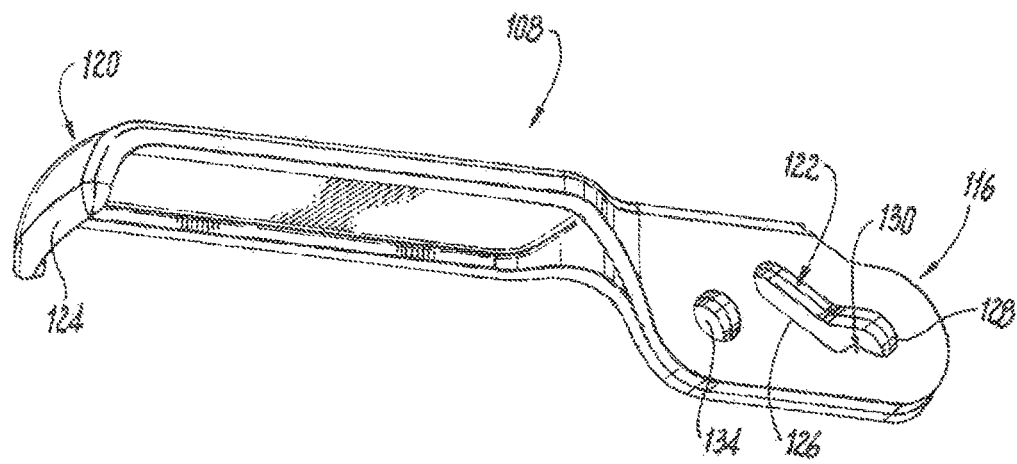
FIG. 4 is a perspective view of a jaw member of the device of FIG. 1, showing the cam slot.
Figure 5:
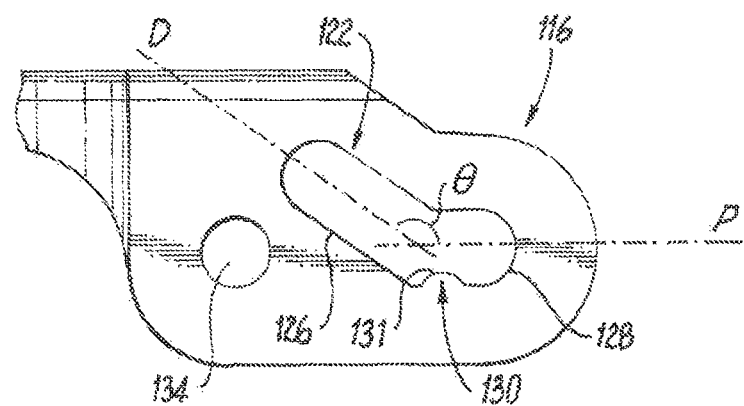
FIG. 5 is a side elevation view of a proximal portion of the jaw member of FIG. 4, showing proximal and distal portions of the cam slot.

As shown in FIGS. 3-5, the distal clip assembly 100 includes a jaw adapter yoke 106 connected to the jaw members 108 via a second pin 118. The jaw members 108 are configured and adapted to rotate about the first pin 110 between an open configuration and a closed configuration. Each jaw member 108 includes a proximal body portion 116 and a distal end effector 120. The proximal body portion 116 of each jaw member 108 includes a respective cam slot 122 configured and adapted to receive the second pin 118. Jaw members 108 are driven by the second pin 118, e.g. a cam pin, moving along the cam slots 122 of the jaw members 108. The second pin 118 is configured and adapted to translate within the cam slots 122 to move axially relative to the distal clip housing 102 and the jaw assembly 104 to move the jaw members 108 between the open configuration where respective distal tips 124 of the jaw members 108 are moved away from one another, the closed configuration where the respective distal tips 124 of the jaw members 108 are approximated towards one another to grasp tissue, and a locked configuration.

Figure 14:
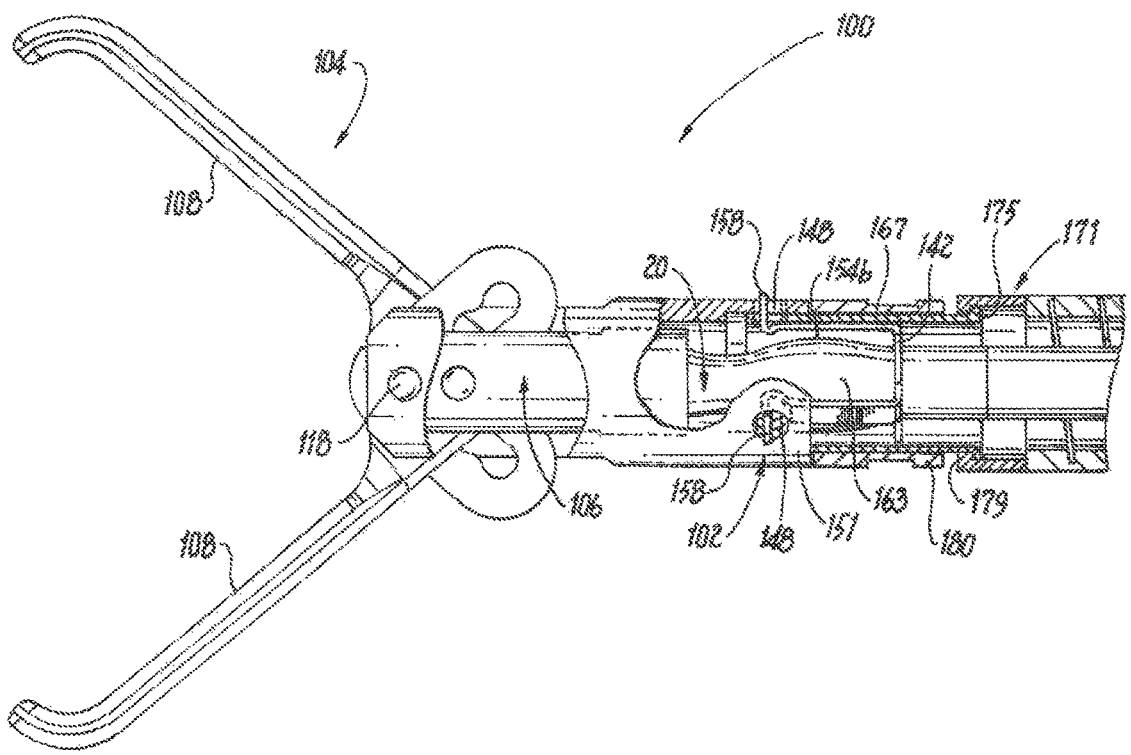
FIG. 14 is a cross-sectional side elevation view of a portion of the device of FIG. 1 with a partial cut-away, showing the jaw members in the open configuration where respective distal tips of the jaw members are moved away from one another to grasp a target area of tissue.
Figure 16:
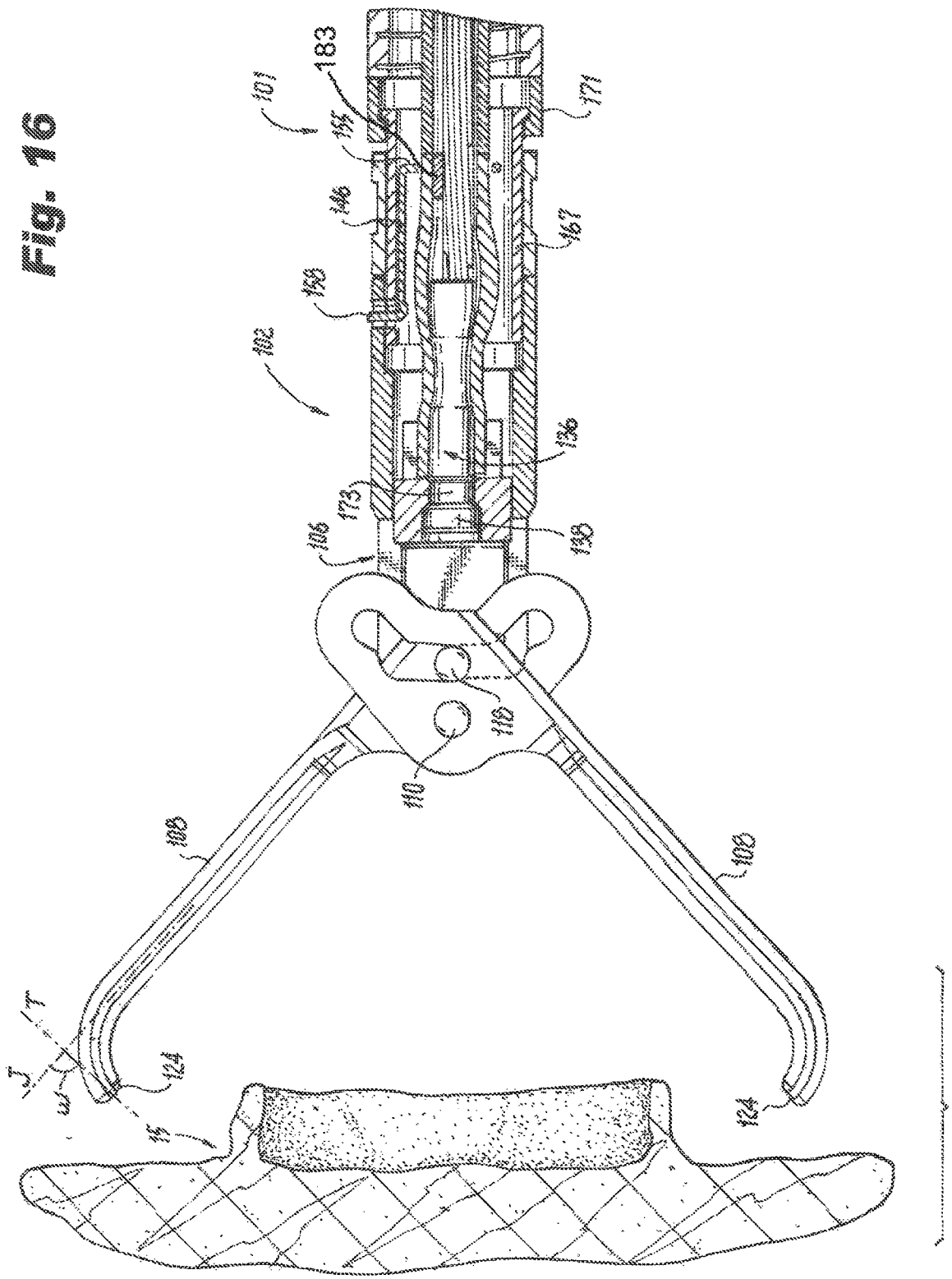
FIG. 16 is a partial cross-sectional side elevation view of a portion of the device of FIG. 1, showing the jaw members in the open configuration where respective distal tips of the jaw members are moved away from one another to grasp a target area of tissue.

With continued reference to FIGS. 3-5, each jaw member 108 includes a pivot aperture 134 configured and adapted to receive the first pin 110. Each jaw member 108 of the jaw assembly 104 is identical to the other member 108, allowing additional economy of scale. The distal end effectors 120 of each jaw member 108 can include at least one pointed peak, multiple peaks, of different or similar size at their distal tips 124. Distal end effectors 120 could also terminate in a combination of pointed peaks and rounded peaks to balance tissue pressure, allowing jaw members 108 to hook tissue with at least one peak and provide atraumatic contact with at least one peak. As shown in FIG. 16, the tooth (or teeth, peaks, etc,) may create an angle ω relative to an axis J of their respective jaw arms 108 between zero and 180 degrees, optimizing the approach angle of distal tips 124 relative to tissue surface. In the embodiment of FIG. 16, the tooth (or teeth, peaks, etc,) may create an angle ω relative to an axis J of their respective jaw arms 108 between zero and 180 degrees, optimizing the approach angle of distal tips 124 relative to tissue surface. In the embodiment of FIG. 14, the angle ω of a tip axis T relative to axis J is approximately 90 degrees. It is contemplated, however, that the angle ω could be at 0 degrees, such that the tip simply extends from axis J, it could be at 45 degrees, or 180 degrees, where the tip is hooked around such that the tip axis T direction is parallel to axis J. The angle and design of jaw members 108 will be optimized for single jaw tissue retention force during manipulation or tissue apposition. The distance between the pivot aperture 134 and the cam slot 122 dictate the moment arm that translates axial translation to jaw rotation/actuation.

Figure 15:
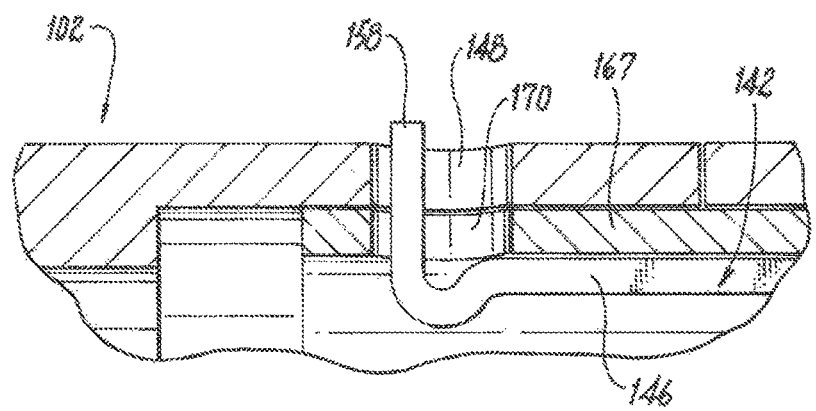
FIG. 15 is a cross-sectional side elevation detail view of a portion of the device of FIG. 1, showing the flanges of the shaft spring engaged with the distal clip housing and the shaft bearing.

As shown in FIGS. 4-5, each cam slot 122 defines a distal portion 126 and a proximal portion 128. The distal portion 126 of each cam slot 122 is angled relative to the proximal portion 128 of each cam slot 122. The proximal portion 128 of each cam slot 122 defines a proximal axis P extending in a first direction. The distal portion 126 of each cam slot 122 defines a distal axis D extending at an oblique angle θ relative to the proximal axis P, and the distal axes D of each cam slot 122 are positioned at opposite angles relative to one another, as shown in FIGS. 14-16. The angle of a respective distal axis D relative to proximal axis P can be fine-tuned to provide optimal tissue clamping force given a user's maximum acceptable input force.

With continued reference to FIGS. 4-5, each cam slot 122 includes a proximal locking neck 130, e.g. a locking feature, projecting into the cam slot 122 defining a proximal locking area 132. The jaw members 108 are in the locked configuration when the second pin 118 is proximal relative to the proximal locking neck 130 in the proximal locking area 132. The proximal locking neck 130 includes a protrusion 131 projecting into the cam slot 122. Lock protrusion 131, e.g. a detent, creates a narrowing of cam slot 122 to form the proximal locking neck 130 that interferes with the outer diameter of the second pin 118 as it moves axially in the proximal direction. The continued axial translation of pin 118 forces a widening of the cam slot 122 in an elastic manner and creates an additional resistance force on the internal drivetrain, e.g. release pin 136 and shaft spring 142. Once the second pin 118 crests the inflection point on the protrusion 131, it will snap into place behind the protrusion 131, effectively locking the jaws in a closed position. The shape of lock protrusion can vary and can be an arcuate, triangular, or slanted feature. Lock protrusion 131 may also be achieved by reversing the slope of cam slot 122 such that it inflects passed the 0 degree orientation with respect to the axis A of the catheter, described in more detail below. Various embodiments for the proximal locking neck are described below in FIGS. 25-29.

Figure 6:
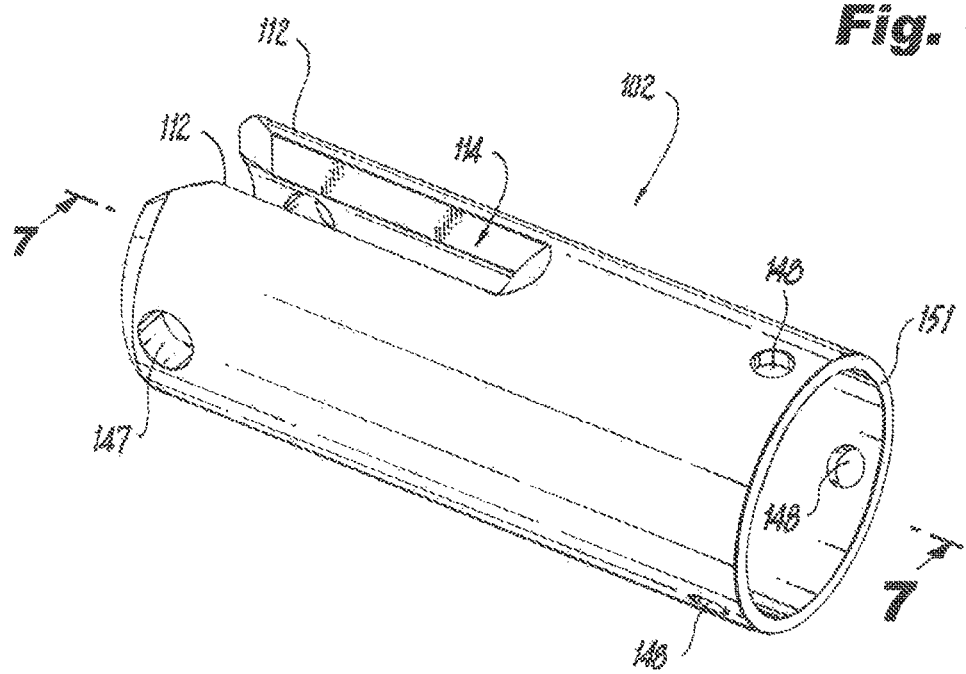
FIG. 6 is a perspective view of a distal clip housing of the device of FIG. 1 from a proximal direction, showing a pair of spaced apart arms defining a slot.
Figure 7:
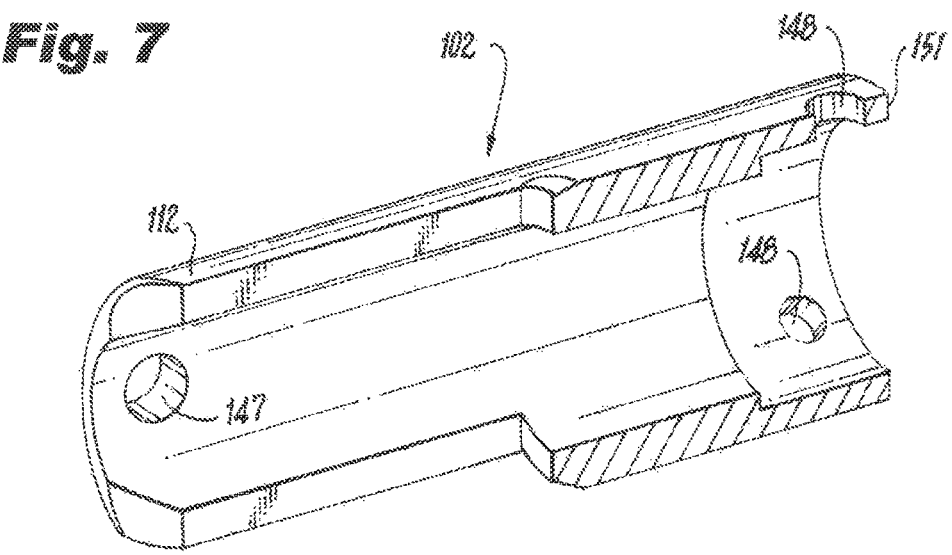
FIG. 7 is a cross-sectional perspective view of the distal clip housing of FIG. 6, showing spaced apart apertures defined about the periphery of a proximal end of the distal clip housing.

As shown in FIGS. 3 and 6-7, the distal clip housing 102 includes a pair of spaced apart arms 112 defining a slot 114 configured and adapted to provide clearance for respective proximal portions 116 of the jaw members 108 to rotate relative the first pin 110. The distal clip housing 102 connects to the shaft spring 142 via apertures 148 spaced apart about a periphery of a proximal end 151 of the distal clip housing 102. Distal clip housing 102 couples to the shaft bearing 167 via shaft spring 142. Flanges 158 from shaft spring 142 intersect transverse apertures 148 in housing 102 and transverse apertures 170 of shaft bearing 167, effectively restraining axial and angular motion in the shaft. A lip 175 of shaft bearing 167 mates with an inward flange 179 of the bearing ring 171 (shown in FIG. 14) to create a joint allowing rotation of shaft bearing 167 relative to bearing ring 171 about longitudinal axis A, but no axial motion along longitudinal axis A. Bearing ring 171 is welded to the distal end 143 elongated catheter body 105 via a flat spring 123 portion of catheter body 105. An outer sleeve 180 is positioned outwards from shaft bearing 167, between distal clip housing 102 and bearing ring 171. The distal clip housing 102 includes a transverse hole 147 oriented perpendicular to the longitudinal axis A to accept the first pin 110, e.g. the pivot pin, which couples to jaw members 108.

As shown in FIGS. 3 and 8A-11, the proximal delivery catheter 101 includes a pin assembly 20 comprised of a release pin 136, e.g. a pin made of silver material, and a release pin housing 163, e.g. a crimped hypotube. The silver material is a substantially ductile material that is resistant to strain hardening and it is contemplated that materials with similar characteristics can be used. The release pin 136 includes a distal portion 138 configured and adapted to be received within the proximal receiving portion 133 of the jaw adapter yoke 106 to transmit axial force to the jaw adapter yoke 106. The release pin 136 includes a neck portion 173 proximal to the distal portion 138, and a proximal portion 140 proximal from the neck portion 173. Release pin 136 has a formed head, e.g. the distal portion 138, that sits inside of a distal counterbore 164 of the jaw adapter yoke 106. The release pin 136 includes a stepped-in outer diameter that forms the neck portion 173, e.g. a notch, having a stress concentration. The neck portion 173 creates a reliable failure point and the soft metal allows for precise break forces to be achieved via a critical diameter. The proximal portion 140 of the pin 136 is crimped inside the inner diameter of the release pin housing 163, described in more detail below. The drive wire 109 is mechanically coupled to a proximal portion of the release pin housing 163 via a laser weld 183 to transmit linear and rotational motion from the drive wire 109 to the release pin housing 163, and in turn to the release pin 136 and then to the jaw adapter yoke 106. The release pin 136 is housed inside jaw housing 102 and release pin housing 163. The release pin 136 is mated inside the release pin housing 163 by one or more mechanical crimps that create a non-round cross section, see FIG. 8B with only the release pin housing 163 and release pin 136 shown. The distal portion 138 of release pin 136 seats inside the counterbore of proximal receiving portion 133 of jaw adapter yoke 106, allowing tension or compression to be transmitted from the proximal drive wire 109 to the jaw members 108.

Figure 9:
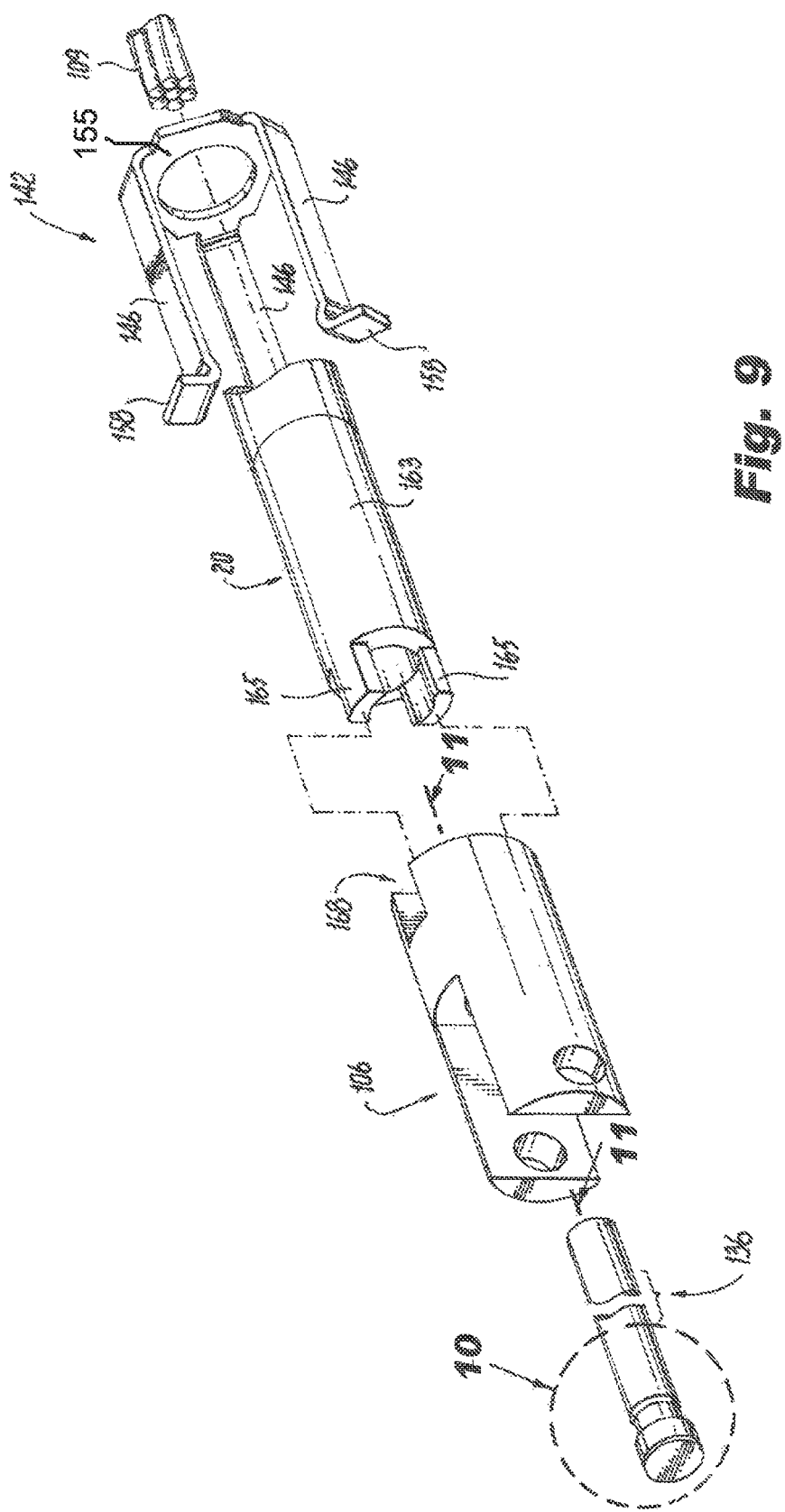
FIG. 9 is a perspective exploded view of a portion of the device of FIG. 1, showing a portion of the release pin housing in an un-crimped state.

With continued reference to FIGS. 8A-9, release pin housing 163 includes torque flanges 165 at a distal end, crimped sections 154a and 154b proximal of the torque flanges, and straight body portion 159 proximal of the torque flanges. The crimped sections 154a and 154b form at least one non-round cross section, shown in FIGS. 8B and 8C. The shaft spring 142 is pulled in a more proximal position than it would be when assembled in order for the details of the release pin 136 and jaw adaptor yoke 106 to be clear. The most proximal non-round cross section, FIG. 8C, has a larger diameter in a plane orthogonal to the longitudinal axis A than the clearance of the inner diameter of the annular portion 155 of shaft spring 142. The straight body section 159 of release pin housing 163 translates freely relative to annular portion 155 during jaw actuation, permitting forward and backwards translation in this range. During clip firing, excessive proximal translation of release pin housing 163 causes the proximal most crimped section 154b to contact shaft spring 142 causing proximal axial translation of shaft spring 142 and disengagement of flanges 158 from distal clip housing 102.

Figure 10:
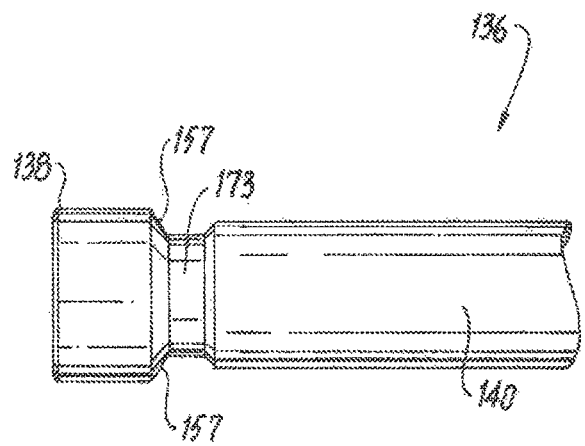
FIG. 10 is a side elevation view of a release pin of the device of FIG. 1, showing a distal portion of the release pin, a proximal portion of the release pin and a neck portion of the release pin between the proximal and distal portions.
Figure 11:
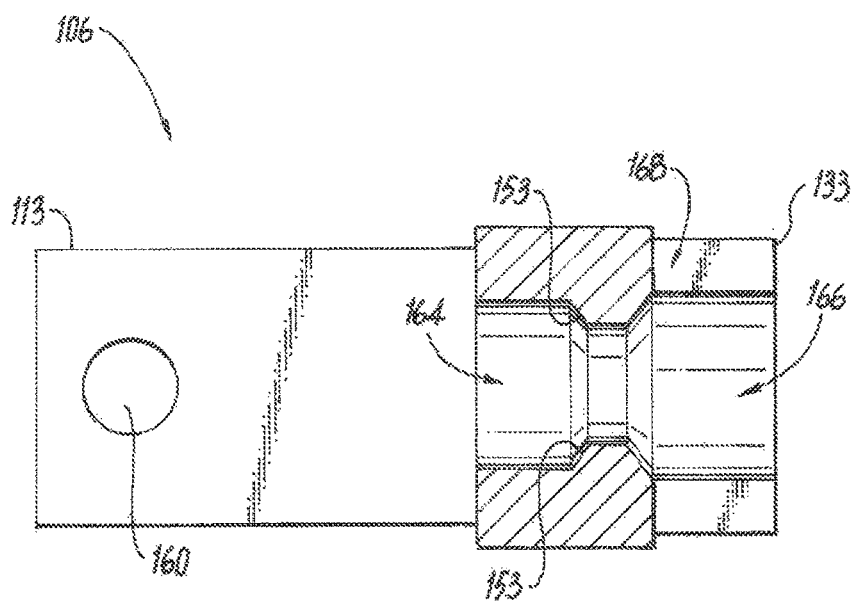
FIG. 11 is a cross-sectional side elevation view of the jaw adapter yoke of the device of FIG. 1, showing the mating surfaces of the jaw adapter yoke.
Figure 12:
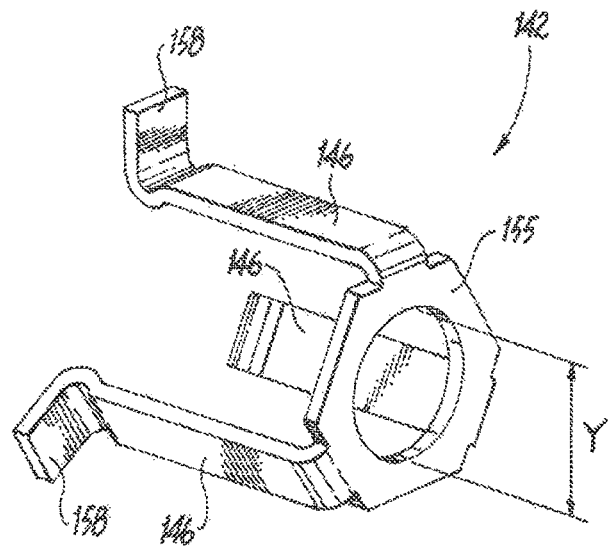
FIG. 12 is a perspective view of a shaft spring of the device of FIG. 1 from a proximal direction, showing the arms of the shaft spring.

As shown in FIGS. 3 and 10-11, the jaw adapter yoke 106 includes a pin aperture 160 and is operatively connected to the jaw members 108 via second pin 118. The jaw adapter yoke 106 is circular component with two arms 113 extending towards the distal end of the yoke 106 that form a slot 161 therebetween. The slot 161 allows the proximal portions 116 of the jaw members 108 rotate around first pin 110. An aperture 160 is formed in each arm 113 and is in a transverse direction to a longitudinal axis of the jaw adapter yoke and the longitudinal axis A of the catheter body 105. The apertures 160 receive the second pin 118 and can be assembled using orbital riveting or laser tack welding. The jaw adapter yoke 106 includes a proximal receiving portion 133 and moves linearly inside of distal clip housing 102 to drive second pin 118 along the cam slots 122. The jaw adapter yoke 106 has an axial through hole comprised of a distal counterbore 164 for mating with a distal portion 138 of the release pin 136, and a proximal counterbore 166 for receiving the proximal portion 140 of the release pin 136. The proximal receiving portion 133 of the jaw adapter yoke 106 has an inner surface that generally conforms with the release pin 136 such that a conical surface 153 on the inner surface of the yoke 106 mate with a conical surface 157 on release pin 136 to transmit axial force from the release pin 136 to the jaw adapter yoke 106. Jaw adapter yoke includes a transverse slot 168 configured and adapted to mate with the torque flanges 165 of the release pin housing 163 to allow for torque transmission directly from the release pin housing 163 to jaw adapter yoke 106 without exerting torsional stress on neck portion 173 of release pin 136.

Figure 13:
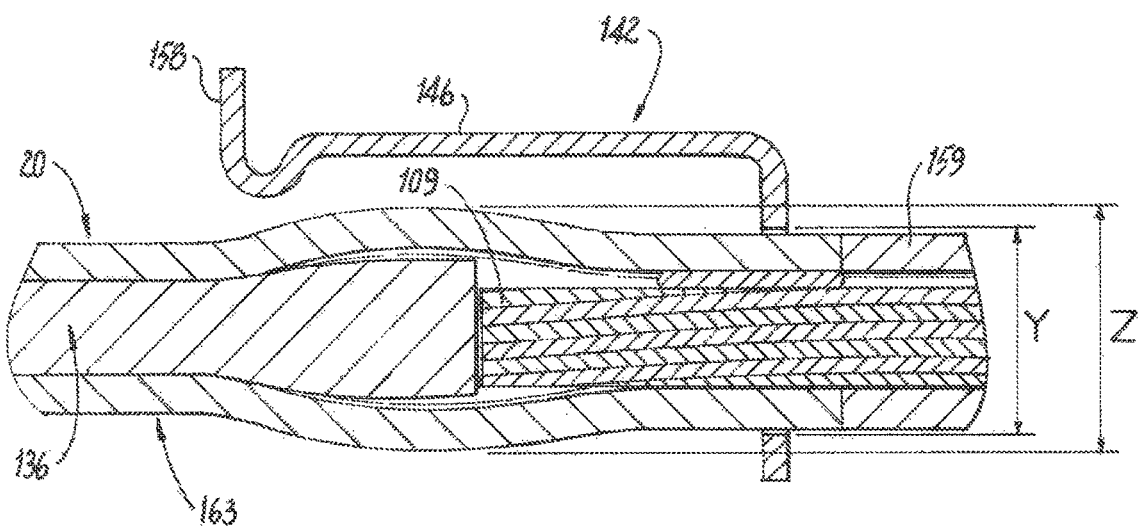
FIG. 13 is a cross-sectional side elevation view of a portion of FIG. 8A, showing the release pin housing and the shaft spring, where shaft spring is shown in a more proximal position than it would be when assembled.

As shown in FIGS. 12-15, the flanges 158 of shaft spring 142 are bent outward at approximately 90-degrees and removably engage with the apertures 148 defined about the periphery of the proximal end 151 of the distal clip housing 102 and apertures 170 of the shaft bearing 167. The release pin assembly 20 (e.g. the release pin 136 and the release pin housing 163) is positioned at least partially within the shaft spring 142. Shaft spring 142 has a through hole in annular portion 155 that allows free axial translation of the straight body section 159 of release pin housing 163 during opening and closure of jaw members 108. Because the maximum dimension Z of the non-round cross section 154b is greater than a diameter Y of the through hole of annular portion 155, as shown in FIG. 13, the outer diameter of release pin housing 163 interferes with the through hole of annular portion 155 upon axial translation in the proximal direction during "firing."

Figure 17:
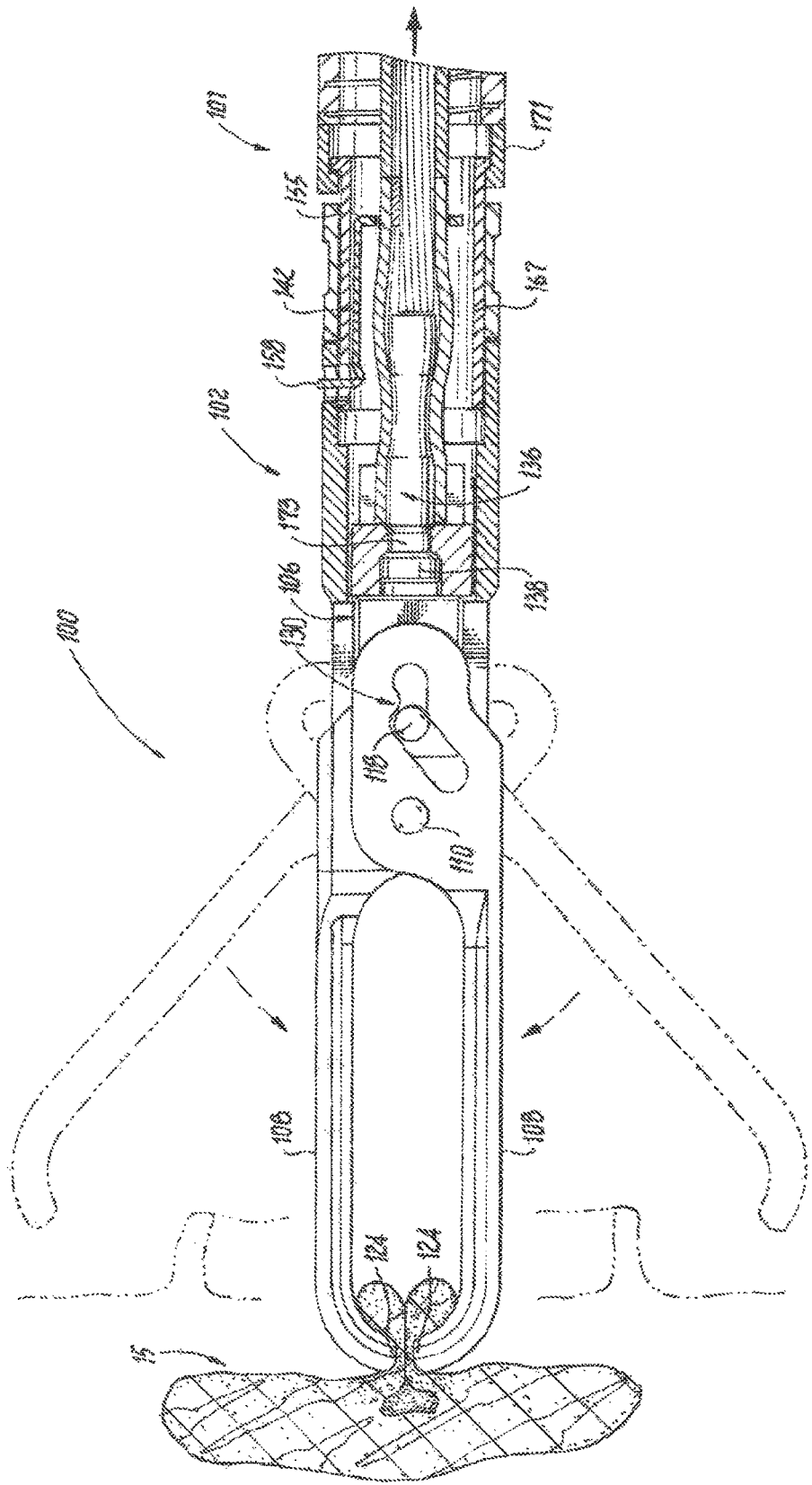
FIG. 17 is a partial cross-sectional side elevation view of a portion of the device of FIG. 1, showing the jaw members in the closed configuration where the respective distal tips of the jaw members are approximated towards one another to grasp tissue.
Figure 18:
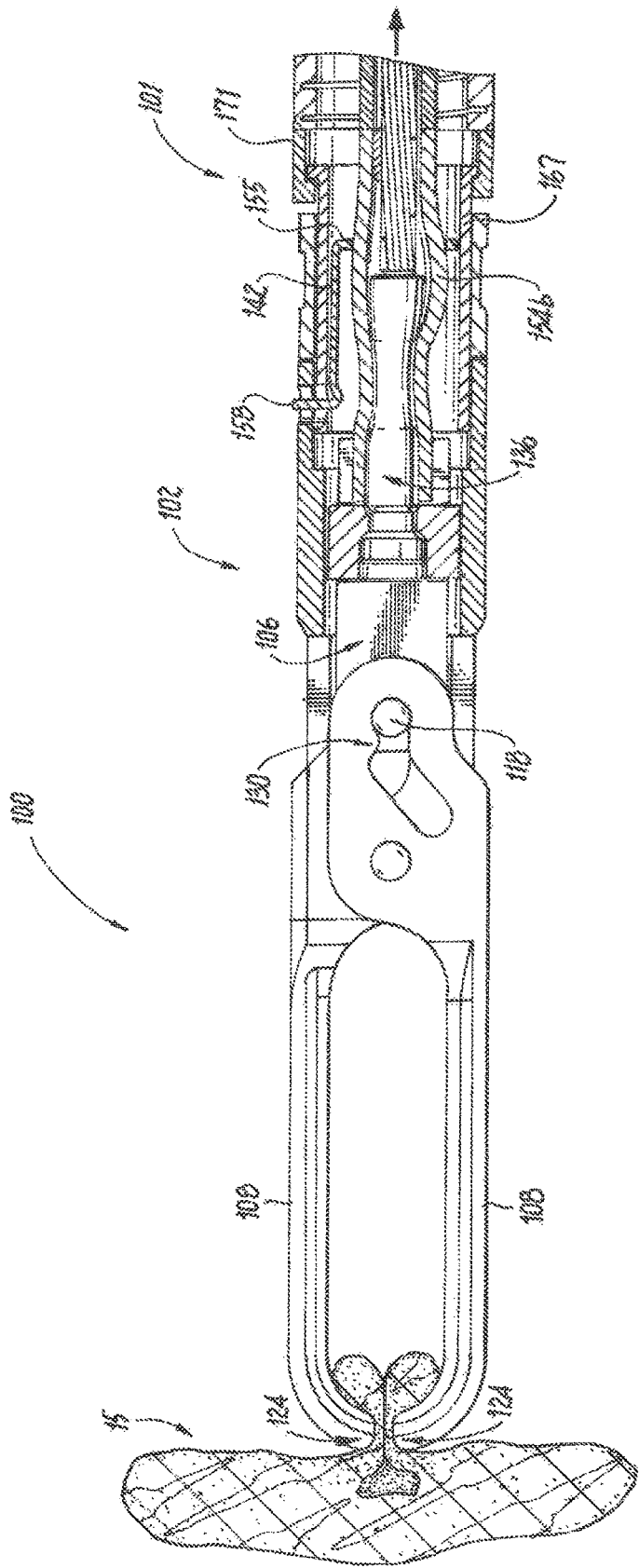
FIG. 18 is a partial cross-sectional side elevation view of a portion of the device of FIG. 1, showing the jaw members in the locked configuration where the second pin is proximal relative to a proximal locking neck.

With reference now to FIGS. 16-20, some of the various configurations of device 10 are shown. In FIG. 16, the device 10 is in the open configuration and the second pin 118 is translated to a distal position within each cam slot 122 such that the distal tips 124 of jaw members 108 are rotated away from one another. In FIG. 17, the device 10 is in a closed configuration and the second pin 118 is translated in a more proximal position within each cam slot 122 relative to the open configuration, but second pin 118 is still distal of the locking neck 130 and the protrusion 131. In the closed configuration, the respective distal tips 124 of the jaw members 108 are approximated towards one another to grasp tissue 15 (but not necessarily in abutment with one another). In FIGS. 18-20, the device 10 is in a locked configuration and the second pin 118 is in a proximal position relative to the locking neck 130 and its respective protrusion 131. In the locked configuration, the second pin 118 is within the proximal locking area 132 of each cam slot 122.

As shown in FIGS. 19-20, once the second pin 118 is in the proximal locking area 132, further axial movement of the pin assembly 20 in a proximal direction (e.g. away from the tissue 15) acts to "fire" the distal clip assembly 100 by releasing the distal clip assembly 100 from the proximal delivery catheter 101. The further linear motion of the release pin 136 in the proximal direction puts the release pin 136 in tension against jaw adapter yoke 106 due to abutment between the conical surface 153 on the inner surface of the yoke 106 and the conical surface 157 on release pin 136. This tension causes shear at the neck portion 173 of release pin, shown schematically by the arrow in FIG. 19, and release from the proximal receiving portion 133. The release force required to detach release pin 136 from the adapter yoke 106 can be tuned by the thickness of the neck portion 173. As shown in FIGS. 18-20, a proximal non-round cross section 154b of release pin housing 163 interferes with an inner diameter of an annular portion 155 of shaft spring 142 when the jaws are fully closed and locked, as shown in FIG. 18. When the drive wire 109 continues to translate backwards, release pin 136 shears at the neck portion 173 due to a stress concentration. Although silver is typically ductile, the stress concentration results in a more sudden, brittle failure at the minor diameter of the neck portion 173. Continued proximal translation forces cause the release pin housing 163 to continue to interfere with the annular portion 155 of shaft spring 142, driving it proximally, resulting in the deflection of flanges 158 and full release of the distal clip assembly 100 from the proximal delivery catheter 101.

With continued reference to FIGS. 19-20, as the release pin 136 continues to move proximally relative to the jaw adapter yoke 106, the shaft spring 142 moves along with the release pin and release pin housing. The motion of shaft spring 142 in the proximal direction creates deflection in the bent over flanges 158 of arms 146, allowing them to pull out of the transverse apertures 148, thereby releasing the distal clip assembly 100. Full disengagement (e.g. "firing") of the distal clip assembly 100 is realized through both the shearing of the release pin 136 and the deflection of flanges 158 of shaft spring 142. The neck portion 173 of the release pin is configured and adapted to shear when an axial force is applied to the release pin in a proximal direction, thereby separating the distal portion from the proximal portion and releasing the proximal portion of the release pin from the distal clip assembly. After firing, proximal delivery catheter 101 can then be removed from the surgical site, leaving the distal clip assembly 100 to function as a short-term implant.

With continued reference to FIGS. 16-20, a single assembly simultaneously shears (release pin 136) and disengages a separate component (of flanges 158) which improves the disconnect mechanism by synchronizing two release events. This also generates an improved disconnect mechanism that enhances the ability to reposition the clip assembly 100 prior to deployment by simplifying the feedback to the user into a single tactile signal. It also makes accidental deployment of the clip assembly 100 less likely, as fewer components are used to realize disengagement. Because there are fewer components, less space is needed in the distal clip assembly 100, allowing for a shorter clip body. The shorter clip "stem" or overall length of deployed clip 100 relative to jaw size is seen as an improvement. Because torque transmission is achieved through a non-deforming, non-frangible linkage (via torque flanges 165 release pin housing 163) angular deflection in the drive train (release pin 136) is relieved and the potential for non-axial forces affecting the release force are minimized. The embodiments herein are described using silver for release pin 136, which is a soft metal allowing for high-precision forming operations that result in highly consistent deployment forces. The soft metal and simplistic design allow for quick mechanical assembly, without the need for welds or more complicated joining technologies.

A method for firing a hemostatic clip assembly, e.g. distal clip assembly 100, includes positioning the distal clip assembly proximate to a target location, e.g. near tissue 15, as shown in FIG. 16, and translating an actuation portion, e.g. actuation portion 115, of a proximal handle assembly, e.g. proximal handle assembly 103, of a proximal delivery catheter, e.g. proximal delivery catheter 101, relative to a grasping portion, e.g. grasping portion 107, of the proximal handle assembly in a proximal direction, thereby translating a drive wire, e.g. drive wire 109. The actuation portion is operatively connected to a jaw adapter yoke, e.g. jaw adapter yoke 106, via a drive wire, e.g. drive wire 109, and a release pin, e.g. release pin 136. Translating the drive wire in the proximal direction includes translating the jaw adapter yoke in the proximal direction. Prior to firing, however, the handle portion of the proximal delivery catheter can be translated in the distal direction to transmit an axial force in the distal direction to the second pin causing the at least one jaw to rotate about the first pin to the open configuration. In this way, the jaw assembly can go between the open position and closed position as much as desired prior to locking and firing. For closing, the linear motion of the jaw adapter yoke transmits the linear motion to a second pin, e.g. second pin 118, positioned within a cam slot, e.g. cam slot 122, of at least one jaw member, e.g. jaw members 108, thereby rotating at least one of the jaw members about the first pin between an open configuration and a closed configuration, as shown in FIGS. 16-17.

The method includes translating the actuation portion in the proximal direction to transmit the linear motion in the proximal direction to the second pin, as shown in FIGS. 17-18, to lock the second pin behind a lock protrusion, e.g. lock protrusion 131, of the cam slot to lock at least one of the jaw members in a locked configuration, as shown in FIG. 18. Translating the actuation portion includes translating the actuation portion further in the proximal direction to transmit further linear motion in the proximal direction to the release pin. The further linear motion in a proximal direction shearing the release pin at a neck portion, as shown in FIG. 19, e.g. neck portion 173, thereby separating a proximal portion, e.g. proximal portion 140, of the release pin from a proximal receiving portion, e.g. proximal receiving portion 133, of a jaw adapter yoke, as shown in FIG. 20.

The axial force on the release pin in the proximal direction causes abutting between an outer diameter of a release pin housing, e.g., release pin housing 163, with an annular portion, e.g. annular portion 155, of a shaft spring, e.g. shaft spring 142, causing the shaft spring to move proximally relative to the distal clip housing and release an outwardly extending flange, e.g. outwardly extending flange 158, of at least one arm, e.g., arms 146, of the shaft spring from an aperture, e.g., aperture 148, of the distal clip housing, as shown in FIGS. 19-20.

In accordance with some embodiments, a method for assembling a release pin assembly, e.g. release pin assembly 20, for use in a proximal delivery catheter, e.g. proximal delivery catheter 101, includes sliding a release pin, e.g. release pin 136, inside of a distal counterbore, e.g. counterbore 164, of a jaw adapter yoke, e.g. jaw adapter yoke 106. The method includes sliding a release pin housing, e.g. release pin housing 163, around a proximal portion, e.g. proximal portion 140, of the pin, and mating torque flanges, e.g. torque flanges 165, of the release pin housing with a transverse slot, e.g. transverse slot 168 of the jaw adapter yoke. The method includes crimping the release pin within the release pin housing by applying one or more mechanical crimps to an outer diameter of the release pin housing proximal to the torque flanges.

Figure 21:
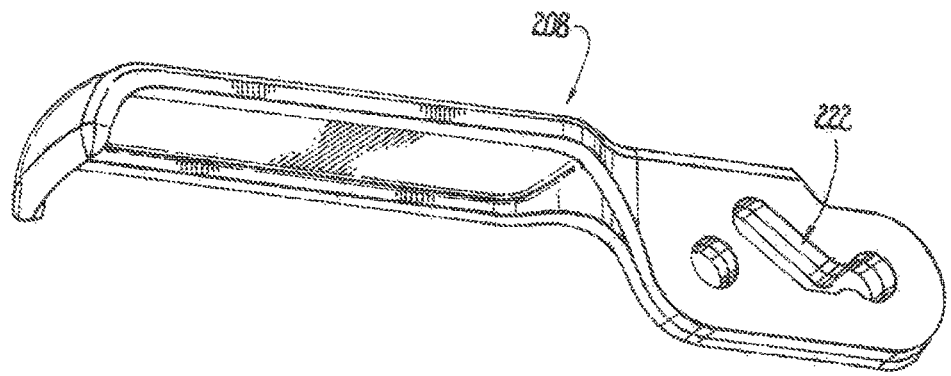
FIG. 21 is a perspective view of another embodiment of a jaw member for use with the device for applying a hemostatic clip assembly of FIG. 1, showing a cam slot.
Figure 22:
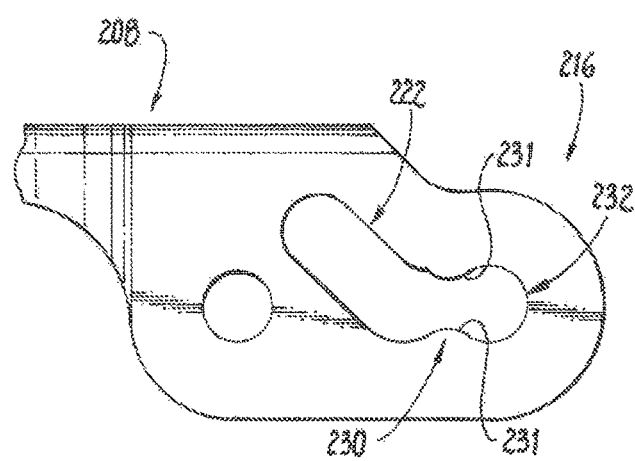
FIG. 22 is a side elevation view of the jaw member of FIG. 20, showing two protrusions in the cam slot.

Referring now to FIGS. 21-25, several different embodiments for the jaw members are described. In FIG. 21-22, an embodiment of a jaw member 208 is shown. Jaw member 208 is similar to jaw members 108 in that it can be used in the jaw assembly 104 and the distal clip assembly 100. Jaw member 208 also includes a distal end effector 220 similar to distal end effector 120. The main difference between jaw member 208 and jaw member 108 is that jaw member 208 includes a cam slot 222 in a proximal portion 216 of the jaw member 208 where the cam slot 222 includes a proximal locking neck 230 with two protrusions 231 projecting into the cam slot 222 defining a proximal locking area 232. Protrusions 231, e.g. detents, interfere with the outer diameter of the of a cam pin, e.g. pin 118. For jaw member 208, the continued axial translation of cam pin 118 forces a widening of the cam slot 222 in an elastic manner and creates an additional resistance force on the internal drivetrain, e.g. release pin 136 and shaft spring 142. Once the cam pin 118 crests the inflection point on the protrusions 231, it will snap into place behind the protrusion 231, effectively locking the jaws in a closed position. Because a drive wire, e.g. drive wire 109, operatively connected to jaw member 208 can only transmit limited compression, a user will not be able to translate sufficient force from a handle assembly, e.g. handle assembly 103, distally to move cam pin 118 out of locking area 132 relative to the protrusions 231 to "unlock" the cam pin.

Figure 23:
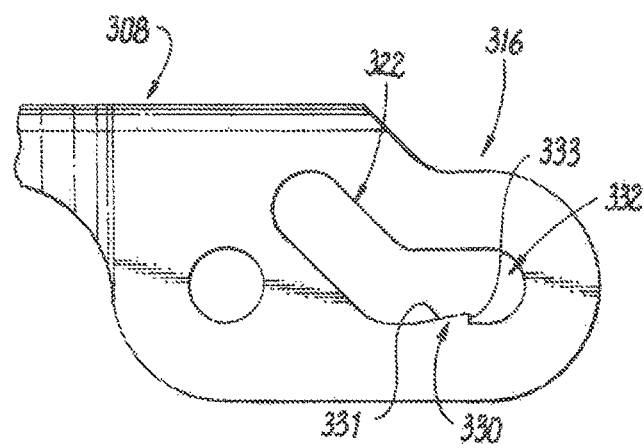
FIG. 23 is a side elevation view of another embodiment of a jaw member for use with the device for applying a hemostatic clip assembly of FIG. 1, showing a tapered portion and a lip in the cam slot.

As shown in FIG. 23, another embodiment of a jaw member 308 is shown. Jaw member 308 is similar to jaw members 108 in that it can be used in the jaw assembly 104 and the distal clip assembly 100. Jaw member 308 also includes a distal end effector similar to distal end effector 120. The main difference between jaw member 308 and jaw member 108 is that jaw member 308 includes a cam slot 322 in a proximal portion 316 of the jaw member 308 having a locking neck 330 formed by a tapered portion 331, e.g. a triangular ramp, having a lip 333. A proximal locking area 332, similar to locking area 132, is defined by the locking neck 330 proximally from the lip 333. This geometry allows an easier transmission of axial force to normal force on the internal walls of cam slot 322, requiring less force to initiate locking. The lip 333 positioned distally relative to the proximal locking area 332 will also prevent axial movement of a cam pin, e.g. cam pin 118, after locking is achieved.

Figure 24:
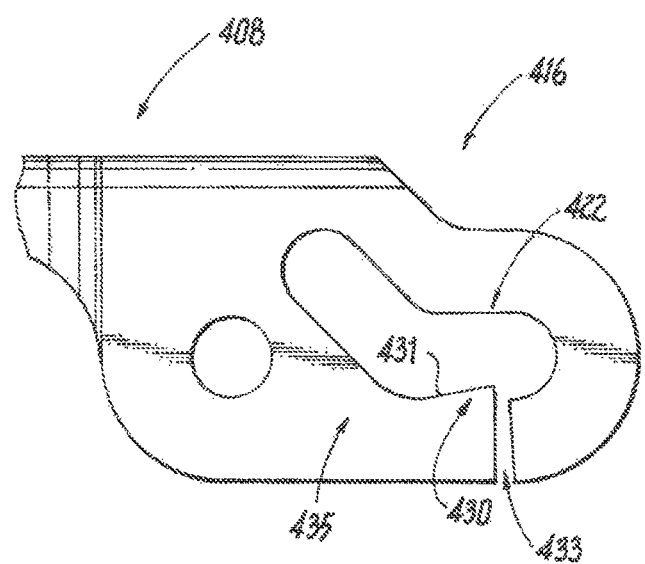
FIG. 24 is a side elevation view of another embodiment of a jaw member for use with the device for applying a hemostatic clip assembly of FIG. 1, showing a slot in the jaw member.

With reference now to FIG. 24, another embodiment of a jaw member 408 is shown. Jaw member 408 is similar to jaw members 108 in that it can be used in the jaw assembly 104 and the distal clip assembly 100. Jaw member 408 also includes a distal end effector similar to distal end effector 120. The main difference between jaw member 408 and jaw member 108 is that jaw member 408 includes a cam slot 422 in a proximal portion 416 of the jaw member 408 having a locking neck 430 formed by a tapered portion 431, e.g. a triangular ramp, terminating in a slot 433. This open contour creates a cantilever lock arm 435 on the bottom wall of cam slot 422. This results in a decreased force required to lock the clip, and results in a higher rate of successful locking in instances where the jaw members 408 are not perfectly parallel to each other, as deflection in the cantilever lock arm 435 can accommodate some axis offset of the jaw members 108. A proximal locking area 432, similar to locking area 132, is defined by the locking neck 430 and positioned proximally from the tapered portion 431.

Figure 25:
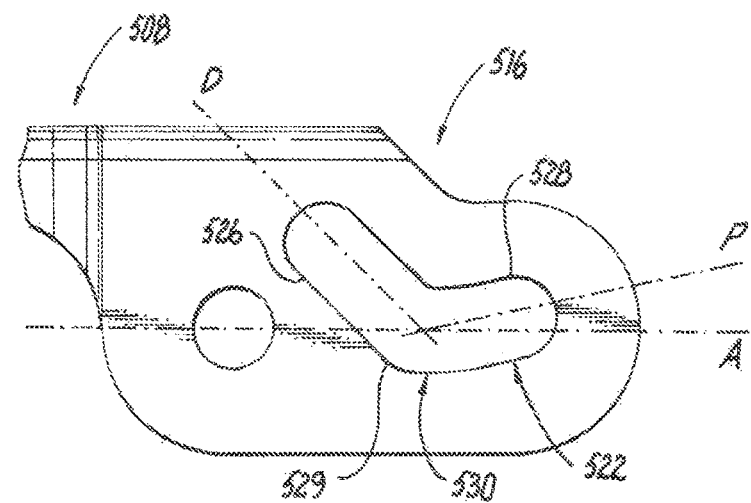
FIG. 25 is a side elevation view of another embodiment of a jaw member for use with the device for applying a hemostatic clip assembly of FIG. 1, showing a reverse slope in the proximal portion of the cam slot.

As shown in FIG. 25, another embodiment of a jaw member 508 is shown. Jaw member 508 is similar to jaw member 108 in that it can be used in the jaw assembly 104 and the distal clip assembly 100. Jaw member 508 also includes a distal end effector similar to distal end effector 120. The main difference between jaw member 508 and jaw member 108 is that jaw member 508 includes a cam slot 522 in a proximal portion 516 of the jaw member 508 having a locking neck 530 formed by a slope reversal on a proximal portion 528 of the cam slot 522. In other words, instead of a proximal axis P of proximal portion 528 being parallel to a longitudinal axis A of a catheter body, e.g. catheter body 105, proximal axis P is angled radially outward relative to axis A resulting in a locking force due to cantilever deflection. In this instance, the user will feel a gradual increase in feedback force, and then a sudden decrease. Once a cam pin, e.g. second pin 118, has crested an inflection point 529 of the pin track (again, relative to the longitudinal axis of the clip body, which is parallel to longitudinal axis A of catheter body at rest) the slope direction changes and begins to force the clip open ever so slightly (0-10 degrees of angulation between jaws. Subsequent unlocking of the jaw members 508 would require equal distal movement of the cam pin relative to a pivot pin, e.g. first pin 110, which is prevented by the spring force required to pass the cam pin over the inflection point during distal translation. Again, an elongate drive wire, e.g. drive wire 109, will not be able to transmit sufficient compressive force to actuate the cam pin distally, effectively locking the clip. The cam slot 522 of jaw member 508 has the as the added benefit of accommodating some amount of tissue thickness between the jaw members 508 without incurring bending stress in the jaw members 508.

Figure 26:
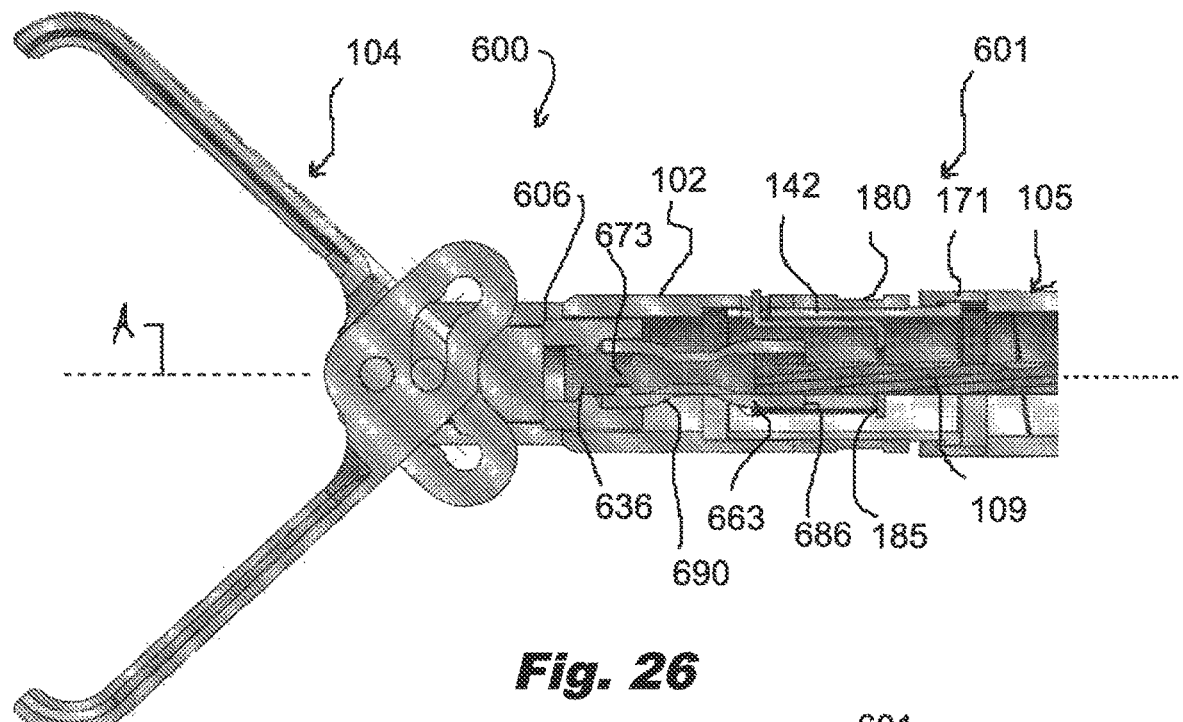
FIG. 26 is a schematic cross-sectional view of a portion of a device for applying a hemostatic clip assembly constructed in accordance with another embodiment of the present disclosure, showing the release pin and release pin housing mated with one crimp.
Figure 27:
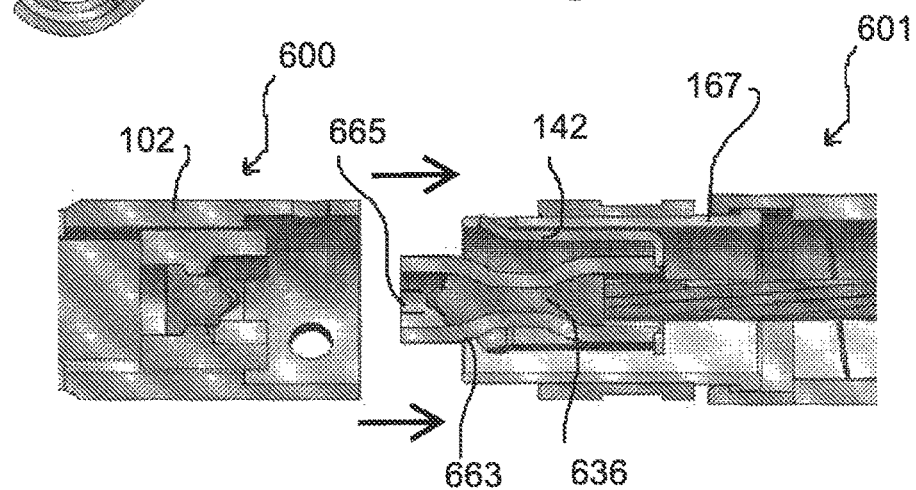
FIG. 27 is a schematic cross-sectional view of a portion of the distal clip assembly and proximal delivery catheter of FIG. 26, showing the abutment between a proximal facing surface of the release pin housing and the distal facing surface of the shaft spring.
Figure 28:
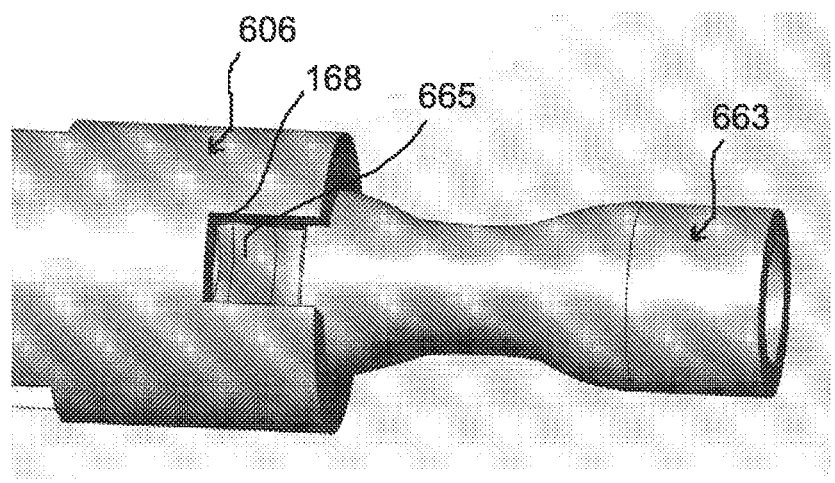
FIG. 28 is a perspective view of the release pin housing and the jaw adapter yoke of FIG. 26, showing the torque flange of the release pin housing engaged with the slot of the jaw adapter yoke.

With reference to FIGS. 26-28, alternative embodiments of distal clip assembly 600 and proximal delivery catheter 601 are shown. In distal clip assembly 600 and proximal delivery catheter 601, a release pin housing 663, a release pin 636 and jaw adapter yoke 606 are used instead of release pin housing 163, release pin 136 and jaw adapter yoke 106. Otherwise, the other components of delivery catheter 601 and distal clip assembly 600 are the same as those of delivery catheter 101 and distal clip assembly 100. Release pin housing 663 includes only one crimped portion 690 about release pin 636 to mechanically connect release pin 636 to housing 663 for common axial translation along and rotation about a longitudinal axis A defined by elongated catheter body 105. In order to drive shaft spring 142 in the proximal direction upon firing, a proximal facing surface 686 of release pin housing 663 interferes with the annular portion by way of abutment. As shown in FIG. 27, the pin housing 663 drives axially in a proximal direction and the proximal facing surface 686 abuts a distal facing surface 185 of annular portion 155 of shaft spring 155, releasing flanges 158. In an un-fired position, release pin housing 663 nests within the inner diameter of yoke 606. In order to transmit torque from the release pin housing 663 to yoke 606 in an un-fired position, an outward extending flange 665 of release pin housing 663 engages with a slot 668 on the perimeter of the yoke 606, as shown in FIG. 28. Similar to release pin housing 163, the control wire 109 is welded to the release pin housing 663 in order to drive the release pin housing 663 axially along and rotate the release pin housing about axis A. Release pin 636 is similar to release pin 136 in that release pin 636 has distal and proximal portions separated by a neck 673.

The methods and systems of the present disclosure, as described above and shown in the drawings, provide for a surgical device with superior properties including simplified user feedback, reduced accidental deployment of the clip assembly and a shorter clip body. While the apparatus and methods of the subject disclosure have been showing and described with reference to embodiments, those skilled in the art will readily appreciate that changes and/or modifications may be made thereto without departing from the spirit and score of the subject disclosure.

What is claimed is:

1. A device for applying a hemostatic clip assembly, comprising:
    a proximal delivery catheter including a proximal handle assembly, an elongated catheter body defining a longitudinal axis and extending distally from the proximal handle assembly, a drive wire movably positioned within the elongated catheter body, a release pin assembly coupled to a distal end of the drive wire, the release pin assembly including a release pin and a release pin housing positioned outward from the release pin, and a shaft spring positioned outward from the release pin housing, wherein the shaft spring includes an annular portion, wherein the release pin housing is configured and adapted to interfere with the annular portion of the shaft spring upon proximal translation of the release pin housing; and
    a distal clip assembly removably connected to a distal end of the elongated catheter body, wherein the proximal delivery catheter is configured and adapted to transmit linear motion along the longitudinal axis and torsion about the longitudinal axis to at least a portion of the distal clip assembly,
    wherein the distal clip assembly includes a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein at least one of the jaw members is configured and adapted to rotate about the first pin between an open configuration and a closed configuration,
    wherein the distal clip assembly includes a second pin connecting between the jaw members and the jaw adapter yoke, wherein each jaw member includes a proximal body portion and a distal end effector, wherein the proximal body portion of each jaw member includes a respective cam slot configured and adapted to receive the second pin and a pivot aperture configured and adapted to receive the first pin,
    wherein the second pin is configured and adapted to translate within each of the respective cam slots to move axially relative to the distal clip housing and the jaw assembly to move the jaw members between the open configuration where respective distal tips of the jaw members are moved away from one another, the closed configuration where the respective distal tips of the jaw members are approximated towards one another to grasp tissue, and a locked configuration, and
    wherein each cam slot includes a proximal locking neck projecting into the cam slot defining a proximal locking area, wherein the jaw members are in the locked configuration when the second pin is proximal relative to the proximal locking neck in the proximal locking area.

2. The device as recited in claim 1, wherein the proximal locking neck includes at least one of a protrusion projecting into the cam slot or a tapered portion.

3. The device as recited in claim 1, wherein the shaft spring includes at least one arm removably coupled to the distal clip housing, wherein the at least one arm includes an outwardly extending flange that removably engages with an aperture defined in a proximal end of the distal clip housing, and wherein the outwardly extending flange of the at least one arm is configured and adapted to release from the aperture of the distal clip housing as the release pin housing moves proximally to move the shaft spring proximally relative to the distal clip housing.

4. A device for applying a hemostatic clip assembly, comprising:
    a proximal delivery catheter including a proximal handle assembly, an elongated catheter body defining a longitudinal axis and extending distally from the proximal handle assembly, a drive wire movably positioned within the elongated catheter body, a release pin assembly coupled to a distal end of the drive wire, the release pin assembly including a release pin and a release pin housing positioned outward from the release pin, and a shaft spring positioned outward from the release pin housing, wherein the shaft spring includes an annular portion, wherein the release pin housing is configured and adapted to interfere with the annular portion of the shaft spring upon proximal translation of the release pin housing; and
    a distal clip assembly removably connected to a distal end of the elongated catheter body, wherein the proximal delivery catheter is configured and adapted to transmit linear motion along the longitudinal axis and torsion about the longitudinal axis to at least a portion of the distal clip assembly,
    wherein the distal clip assembly includes a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein at least one of the jaw members is configured and adapted to rotate about the first pin between an open configuration and a closed configuration,
    wherein the distal clip assembly includes a second pin connecting between the jaw members and the jaw adapter yoke, wherein each jaw member includes a proximal body portion and a distal end effector, wherein the proximal body portion of each jaw member includes a respective cam slot configured and adapted to receive the second pin and a pivot aperture configured and adapted to receive the first pin,
    wherein the second pin is configured and adapted to translate within each of the respective cam slots to move axially relative to the distal clip housing and the jaw assembly to move the jaw members between the open configuration where respective distal tips of the jaw members are moved away from one another, the closed configuration where the respective distal tips of the jaw members are approximated towards one another to grasp tissue, and a locked configuration, and wherein each cam slot defines a distal portion and a proximal portion, wherein the distal portion of each cam slot is angled relative to the proximal portion of each cam slot.

5. The device as recited in claim 4, wherein the proximal portion of each cam slot defines a proximal axis extending in a first direction, the distal portion of each cam slot defines a distal axis extending at an oblique angle relative to the proximal axis, and the distal axes of each cam slot are positioned at opposite angles relative to one another.

6. The device as recited in claim 4, wherein the shaft spring includes at least one arm removably coupled to the distal clip housing, wherein the at least one arm includes an outwardly extending flange that removably engages with an aperture defined in a proximal end of the distal clip housing, and wherein the outwardly extending flange of the at least one arm is configured and adapted to release from the aperture of the distal clip housing as the release pin housing moves proximally to move the shaft spring proximally relative to the distal clip housing.

7. A device for applying a hemostatic clip assembly, comprising:
  a proximal delivery catheter including a proximal handle assembly, an elongated catheter body defining a longitudinal axis and extending distally from the proximal handle assembly, a drive wire movably positioned within the elongated catheter body, a release pin assembly coupled to a distal end of the drive wire, the release pin assembly including a release pin and a release pin housing positioned outward from the release pin, and a shaft spring positioned outward from the release pin housing, wherein the shaft spring includes an annular portion, wherein the release pin housing is configured and adapted to interfere with the annular portion of the shaft spring upon proximal translation of the release pin housing; and
  a distal clip assembly removably connected to the a distal end of the elongated catheter body, wherein the proximal delivery catheter is configured and adapted to transmit linear motion along the longitudinal axis and torsion about the longitudinal axis to at least a portion of the distal clip assembly,
  wherein the distal clip assembly includes a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein at least one of the jaw members is configured and adapted to rotate about the first pin between an open configuration and a closed configuration, and
  wherein the jaw adapter yoke includes a proximal receiving portion and the release pin includes a distal portion configured and adapted to be received within the proximal receiving portion of the jaw adapter yoke to transmit axial and rotational force from the drive wire to the jaw adapter yoke.

8. The device as recited in claim 7, wherein the drive wire is coupled to a proximal portion of the release pin to transmit linear and rotational motion from the drive wire to the jaw adapter yoke.

9. The device as recited in claim 8, wherein the proximal handle assembly includes an actuation portion coupled to a proximal end of the drive wire, and a grasping portion, wherein the actuation portion is configured and adapted to translate relative to the grasping portion to apply axial force to the drive wire.

10. The device as recited in claim 7, wherein the release pin comprises a silver material.

11. The device as recited in claim 7, wherein the distal clip assembly includes a second pin connecting between the jaw members and the jaw adapter yoke, wherein each jaw member includes a proximal body portion and a distal end effector, wherein the proximal body portion of each jaw member includes a respective cam slot configured and adapted to receive the second pin and a pivot aperture configured and adapted to receive the first pin, and
  wherein the second pin is configured and adapted to translate within the cam slots to move axially relative to the distal clip housing and the jaw assembly to move the jaw members between the open configuration where respective distal tips of the jaw members are moved away from one another, the closed configuration where the respective distal tips of the jaw members are approximated towards one another to grasp tissue, and a locked configuration.

12. The device as recited in claim 7, wherein the shaft spring includes at least one arm removably coupled to the distal clip housing, wherein the at least one arm includes an outwardly extending flange that removably engages with an aperture defined in a proximal end of the distal clip housing, and wherein the outwardly extending flange of the at least one arm is configured and adapted to release from the aperture of the distal clip housing as the release pin housing moves proximally to move the shaft spring proximally relative to the distal clip housing.

13. A device for applying a hemostatic clip assembly, comprising:
  a proximal delivery catheter including a proximal handle assembly, an elongated catheter body defining a longitudinal axis and extending distally from the proximal handle assembly, a drive wire movably positioned within the elongated catheter body, a release pin assembly coupled to a distal end of the drive wire, the release pin assembly including a release pin and a release pin housing positioned outward from the release pin, and a shaft spring positioned outward from the release pin housing, wherein the shaft spring includes an annular portion, wherein the release pin housing is configured and adapted to interfere with the annular portion of the shaft spring upon proximal translation of the release pin housing; and
  a distal clip assembly removably connected to the-a distal end of the elongated catheter body, wherein the proximal delivery catheter is configured and adapted to transmit linear motion along the longitudinal axis and torsion about the longitudinal axis to at least a portion of the distal clip assembly,
  wherein the release pin housing has at least one non-circular cross-section portion, wherein the annular portion of the shaft spring is positioned around the release pin housing proximal to the at least one non-circular cross-section portion, wherein the non-circular cross-section portion is configured and adapted to interfere with the annular portion of the shaft spring upon proximal translation of the release pin housing.

14. The device as recited in claim 13, wherein the release pin comprises a silver material.

15. The device as recited in claim 13, wherein the distal clip assembly includes a second pin connecting between the jaw members and the jaw adapter yoke, wherein each jaw member includes a proximal body portion and a distal end effector, wherein the proximal body portion of each jaw member includes a respective cam slot configured and adapted to receive the second pin and a pivot aperture configured and adapted to receive the first pin, and wherein the second pin is configured and adapted to translate within the cam slots to move axially relative to the distal clip housing and the jaw assembly to move the jaw members between the open configuration where respective distal tips of the jaw members are moved away from one another, the closed configuration where the respective distal tips of the jaw members are approximated towards one another to grasp tissue, and a locked configuration.

16. The device as recited in claim 13, wherein the distal clip assembly includes a distal clip housing, wherein the shaft spring includes at least one arm removably coupled to the distal clip housing, wherein the at least one arm includes an outwardly extending flange that removably engages with an aperture defined in a proximal end of the distal clip housing, and wherein the outwardly extending flange of the at least one arm is configured and adapted to release from the aperture of the distal clip housing as the release pin housing moves proximally to move the shaft spring proximally relative to the distal clip housing.

17. The device as recited in claim 13, wherein the distal clip assembly includes a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein at least one of the jaw members is configured and adapted to rotate about the first pin between an open configuration and a closed configuration, and wherein the distal clip housing includes a pair of spaced apart arms defining a slot configured and adapted to provide clearance for respective proximal portions of the jaw members to rotate relative the first pin.

18. A device for applying a hemostatic clip assembly, comprising:

a proximal delivery catheter including a proximal handle assembly, an elongated catheter body defining a longitudinal axis and extending distally from the proximal handle assembly, a drive wire movably positioned within the elongated catheter body, a release pin assembly coupled to a distal end of the drive wire, the release pin assembly including a release pin and a release pin housing positioned outward from the release pin, and a shaft spring positioned outward from the release pin housing, wherein the shaft spring includes an annular portion, wherein the release pin housing is configured and adapted to interfere with the annular portion of the shaft spring upon proximal translation of the release pin housing; and a distal clip assembly removably connected to a distal end of the elongated catheter body, wherein the proximal delivery catheter is configured and adapted to transmit linear motion along the longitudinal axis and torsion about the longitudinal axis to at least a portion of the distal clip assembly, wherein the distal clip assembly includes a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein at least one of the jaw members is configured and adapted to rotate about the first pin between an open configuration and a closed configuration, and wherein the release pin includes a distal portion, a proximal portion, and a neck portion therebetween, wherein the distal portion of the release pin is configured and adapted to be received within a bore of the jaw adapter yoke to transmit axial force to the jaw adapter yoke.

19. The device as recited in claim 18, wherein the neck portion of the release pin is configured and adapted to shear when an axial force is applied to the release pin in a proximal direction, thereby separating the distal portion of the release pin from the proximal portion of the release pin, and releasing the proximal portion of the release pin from the distal clip assembly.

20. The device as recited in claim 18, wherein the neck portion of the release pin has a smaller diameter than the proximal portion of the release pin and the distal portion of the release pin, thereby configured and adapted to create a stress concentration to limit elongation during a shear.

21. The device as recited in claim 18, wherein the release pin comprises a silver material.

22. The device as recited in claim 18, wherein the distal clip assembly includes a second pin connecting between the jaw members and the jaw adapter yoke, wherein each jaw member includes a proximal body portion and a distal end effector, wherein the proximal body portion of each jaw member includes a respective cam slot configured and adapted to receive the second pin and a pivot aperture configured and adapted to receive the first pin, and wherein the second pin is configured and adapted to translate within the cam slots to move axially relative to the distal clip housing and the jaw assembly to move the jaw members between the open configuration where respective distal tips of the jaw members are moved away from one another, the closed configuration where the respective distal tips of the jaw members are approximated towards one another to grasp tissue, and a locked configuration.

23. The device as recited in claim 18, wherein the shaft spring includes at least one arm removably coupled to the distal clip housing, wherein the at least one arm includes an outwardly extending flange that removably engages with an aperture defined in a proximal end of the distal clip housing, and wherein the outwardly extending flange of the at least one arm is configured and adapted to release from the aperture of the distal clip housing as the release pin housing moves proximally to move the shaft spring proximally relative to the distal clip housing.

* * * * *